(12) United States Patent
Kohatsu et al.

(10) Patent No.: US 12,042,007 B2
(45) Date of Patent: **\*Jul. 23, 2024**

(54) ARTICLE OF FOOTWEAR COMPRISING A SOLE MEMBER WITH GEOMETRIC PATTERNS

(71) Applicant: NIKE, Inc., Beaverton, OR (US)

(72) Inventors: Shane S. Kohatsu, Portland, OR (US); Christopher S. Cook, Portland, OR (US); Bret Schoolmeester, Banks, OR (US)

(73) Assignee: NIKE, Inc., Beaverton, OR (US)

( \* ) Notice: Subject to any disclaimer, the term of this patent is extended or adjusted under 35 U.S.C. 154(b) by 0 days.

This patent is subject to a terminal disclaimer.

(21) Appl. No.: 18/068,931

(22) Filed: Dec. 20, 2022

(65) Prior Publication Data

US 2023/0122676 A1    Apr. 20, 2023

Related U.S. Application Data

(60) Continuation of application No. 17/201,581, filed on Mar. 15, 2021, now Pat. No. 11,553,756, which is a
(Continued)

(51) Int. Cl.
*A43B 3/00* (2022.01)
*A43B 7/14* (2022.01)
(Continued)

(52) U.S. Cl.
CPC .......... *A43B 13/186* (2013.01); *A43B 3/0042* (2013.01); *A43B 7/1485* (2013.01);
(Continued)

(58) Field of Classification Search
CPC ... A43B 3/0036; A43B 3/0042; A43B 7/1405; A43B 7/1485; A43B 13/141; A43B 13/18; A43B 13/181; A43B 13/186
(Continued)

(56) References Cited

U.S. PATENT DOCUMENTS 1,785,410 A    12/1930  Gilkerson
2,150,057 A    3/1939   Fisch
(Continued)

FOREIGN PATENT DOCUMENTS

EP    1795083 A1 \*  6/2007  ........... A43B 13/125
EP    3217930 A1     9/2017
(Continued)

OTHER PUBLICATIONS

Aug. 31, 2016-(WO) International Search Report and Written Opinion-App PCT/US2016/032005.
Jul. 8, 2021-(Ep) ESR-App. No. 21166126.9.

*Primary Examiner* — Sharon M Prange
(74) *Attorney, Agent, or Firm* — Banner & Witcoff, Ltd.

(57) ABSTRACT

An article of footwear includes an upper and a sole structure with a sole member. The sole member can include a set of apertures that is formed along various surfaces of the sole member. The sole member can be manufactured using a customized cushioning sole system, forming generally circular patterns throughout the sole member. A user's foot morphology and/or preferences may be used to design the sole member.

16 Claims, 21 Drawing Sheets

Related U.S. Application Data continuation of application No. 16/220,456, filed on Dec. 14, 2018, now Pat. No. 10,973,280, which is a division of application No. 14/722,826, filed on May 27, 2015, now Pat. No. 10,206,456.

(51) Int. Cl.

| | | |
|---|---|---|
| *A43B 7/1485* | (2022.01) | |
| *A43B 13/18* | (2006.01) | |
| *A43D 1/02* | (2006.01) | |
| *A61B 5/103* | (2006.01) | |

(52) U.S. Cl.
CPC ............... *A43D 1/02* (2013.01); *A43D 1/025* (2013.01); *A61B 5/1036* (2013.01); *A43D 2200/60* (2013.01)

(58) Field of Classification Search
USPC .............................................. 36/25 R, 27, 28
See application file for complete search history.

(56) References Cited

U.S. PATENT DOCUMENTS

| | | | |
|---|---|---|---|
| 2,885,797 A | 5/1959 | Chrencik | |
| 2,983,056 A | 5/1961 | Murawski | |
| 3,087,261 A | 4/1963 | Russell | |
| 3,253,355 A | 5/1966 | Menken | |
| 3,418,731 A | 12/1968 | Anciaux | |
| 3,785,646 A | 1/1974 | Ruskin | |
| 4,223,455 A * | 9/1980 | Vermeulen | A43B 13/20 |
| | | | 36/29 |
| 4,235,026 A | 11/1980 | Plagenhoef | |
| 4,237,627 A * | 12/1980 | Turner | A43B 13/187 |
| | | | 36/129 |
| 4,494,322 A | 1/1985 | Klagmann | |
| 4,523,393 A | 6/1985 | Inohara | |
| 4,525,940 A | 7/1985 | Mochizuki | |
| 4,624,061 A | 11/1986 | Wezel et al. | |
| 4,670,997 A | 6/1987 | Beekman | |
| 4,956,927 A | 9/1990 | Misevich et al. | |
| 5,044,096 A | 9/1991 | Polegato | |
| 5,068,983 A * | 12/1991 | Marc | A43B 17/02 |
| | | | 36/43 |
| 5,699,627 A | 12/1997 | Castro | |
| 5,799,413 A * | 9/1998 | Argyris | A43B 7/146 |
| | | | 36/3 R |
| 6,082,824 A | 7/2000 | Chow | |
| 6,266,896 B1 | 7/2001 | Liu | |
| 6,675,502 B1 | 1/2004 | Chen | |
| 6,874,252 B2 | 4/2005 | Nakano | |
| 7,032,328 B2 | 4/2006 | Wilson et al. | |
| 7,216,092 B1 | 5/2007 | Weber et al. | |
| 7,434,338 B2 | 10/2008 | Pfander | |
| 7,464,490 B2 | 12/2008 | Lebo | |
| 7,475,497 B2 | 1/2009 | Hoffer et al. | |
| 7,607,241 B2 | 10/2009 | McDonald et al. | |
| 7,707,746 B2 | 5/2010 | Dean | |
| 7,941,938 B2 | 5/2011 | Yu et al. | |
| 8,479,414 B2 * | 7/2013 | Baker | A43B 7/148 |
| | | | 36/43 |
| 8,584,379 B2 | 11/2013 | Baucom et al. | |
| 8,713,819 B2 | 5/2014 | Auger et al. | |
| 8,732,982 B2 | 5/2014 | Sullivan et al. | |
| 8,752,307 B2 | 6/2014 | Cooper et al. | |
| 9,192,211 B2 * | 11/2015 | Lafortune | A43B 13/187 |
| 9,635,897 B2 | 5/2017 | Prust et al. | |
| 2001/0032400 A1 | 10/2001 | Brooks | |
| 2002/0152640 A1 | 10/2002 | Wu | |
| 2003/0217485 A1 | 11/2003 | Oishi et al. | |
| 2004/0016148 A1 | 1/2004 | Chen | |
| 2004/0024645 A1 | 2/2004 | Potter et al. | |
| 2004/0159015 A1 | 8/2004 | Dennis et al. | |
| 2004/0168354 A1 | 9/2004 | Nguyen | |
| 2006/0156579 A1 * | 7/2006 | Hoffer | A43B 13/186 |
| | | | 36/28 |
| 2009/0178299 A1 * | 7/2009 | Lafortune | A43B 21/26 |
| | | | 36/35 B |
| 2010/0126041 A1 | 5/2010 | Francis | |
| 2011/0061263 A1 | 3/2011 | Everz-Vaz | |
| 2011/0099850 A1 | 5/2011 | van Dyck | |
| 2011/0162234 A1 | 7/2011 | Dean | |
| 2012/0180335 A1 * | 7/2012 | Mahoney | A43B 23/027 |
| | | | 36/28 |
| 2012/0180336 A1 * | 7/2012 | Sullivan | A43B 13/188 |
| | | | 36/31 |
| 2013/0160223 A1 | 6/2013 | Bier et al. | |
| 2013/0219746 A1 | 8/2013 | Chiu | |
| 2013/0258085 A1 | 10/2013 | Leedy et al. | |
| 2014/0182049 A1 * | 7/2014 | Prust | A42B 3/12 |
| | | | 36/43 |
| 2014/0182170 A1 | 7/2014 | Wawrousek et al. | |
| 2014/0223777 A1 | 8/2014 | Whiteman et al. | |
| 2014/0290094 A1 | 10/2014 | Miner | |
| 2014/0366399 A1 | 12/2014 | Wakeland et al. | |
| 2017/0318900 A1 * | 11/2017 | Charlesworth | B33Y 50/02 |

FOREIGN PATENT DOCUMENTS

| | | |
|---|---|---|
| GB | 1512745 A | 6/1978 |
| WO | 2014100462 A1 | 6/2014 |

* cited by examiner

# ARTICLE OF FOOTWEAR COMPRISING A SOLE MEMBER WITH GEOMETRIC PATTERNS

RELATED APPLICATION DATA

This application is: (a) a continuation application based on co-pending U.S. patent application Ser. No. 17/201,581 titled "Article of Footwear Comprising a Sole Member with Geometric Patterns," filed Mar. 15, 2021, which application is (b) a continuation application based on U.S. patent application Ser. No. 16/220,456 titled "Article of Footwear Comprising a Sole Member with Geometric Patterns," filed Dec. 14, 2018 (now U.S. Pat. No. 10,973,280 B2 granted Apr. 13, 2021), which is (c) a divisional application based on U.S. patent application Ser. No. 14/722,826 titled "Article of Footwear Comprising a Sole Member with Geometric Patterns," filed May 27, 2015 (now U.S. Pat. No. 10,206,456 B2, granted Feb. 19, 2019). Each of U.S. patent application Ser. Nos. 17/201,581, 16/220,456 and 14/722,826 is incorporated by reference herein entirely.

BACKGROUND

The present embodiments relate generally to articles of footwear, and in particular to articles with cushioning provisions and methods of making such articles.

Articles of footwear generally include two primary elements: an upper and a sole structure. The upper is often formed from a plurality of material elements (e.g., textiles, polymer sheet layers, foam layers, leather, synthetic leather) that are stitched or adhesively bonded together to form a void on the interior of the footwear for comfortably and securely receiving a foot. More particularly, the upper forms a structure that extends over instep and toe areas of the foot, along medial and lateral sides of the foot, and around a heel area of the foot. The upper may also incorporate a lacing system to adjust the fit of the footwear, as well as permitting entry and removal of the foot from the void within the upper. In addition, the upper may include a tongue that extends under the lacing system to enhance the adjustability and comfort of the footwear, and the upper may incorporate a heel counter.

The sole structure is secured to a lower portion of the upper so as to be positioned between the foot and the ground. In athletic footwear, for example, the sole structure includes a midsole and an outsole. The various sole structure components may be formed from a polymer foam material that attenuates ground reaction forces (i.e., provides cushioning) during walking, running, and other ambulatory activities. The sole structure may also include fluid-filled chambers, plates, moderators, or other elements that further attenuate forces, enhance stability, or influence the motions of the foot, for example.

SUMMARY

In one aspect, the present disclosure is directed to a sole member for an article of footwear, comprising the sole member, the sole member including an outer surface, and the outer surface comprising an upper surface and a lower surface. Furthermore, the sole member has an interior portion, where the interior portion is disposed between the upper surface and the lower surface. The sole member includes at least a first set of apertures, where at least one of the apertures of the first set of apertures is a blind-hole aperture. The first set of apertures is disposed along a portion of the outer surface of the sole member, and each aperture of the first set of apertures has a length extending through a portion of the interior portion of the sole member. The first set of apertures is arranged along the outer surface of the sole member in a generally circular first pattern.

In another aspect, the present disclosure is directed to a sole member for an article of footwear, comprising the sole member, the sole member including an outer surface, and the outer surface comprising an upper surface and a lower surface. The sole member has at least a first set of apertures, where at least one of the first set of apertures is a blind-hole aperture. The first set of apertures is disposed along a portion of the outer surface of the sole member to form a generally circular first pattern, and each aperture of the first set of apertures is disposed at a first radial distance from a center of the first pattern.

In another aspect, the present disclosure is directed to a method for customizing a cushioning sole system for an article of footwear, the method comprising obtaining information about a pressure distribution of a wearer's foot, and producing a first pattern comprising a first set of apertures disposed around a center of the first pattern. The method further includes generating instructions to form the first pattern in a sole member, and executing the instructions to form the first set of apertures in the sole member, wherein each aperture of the first set of apertures is disposed at a first radial distance from the center.

Other systems, methods, features, and advantages of the embodiments will be, or will become, apparent to one of ordinary skill in the art upon examination of the following figures and detailed description. It is intended that all such additional systems, methods, features, and advantages be included within this description and this summary, be within the scope of the embodiments, and be protected by the following claims.

BRIEF DESCRIPTION OF THE DRAWINGS

The embodiments can be better understood with reference to the following drawings and description. The components in the figures are not necessarily to scale, emphasis instead being placed upon illustrating the principles of the embodiments. Moreover, in the figures, like reference numerals designate corresponding parts throughout the different views.

DETAILED DESCRIPTION

Figure 1:
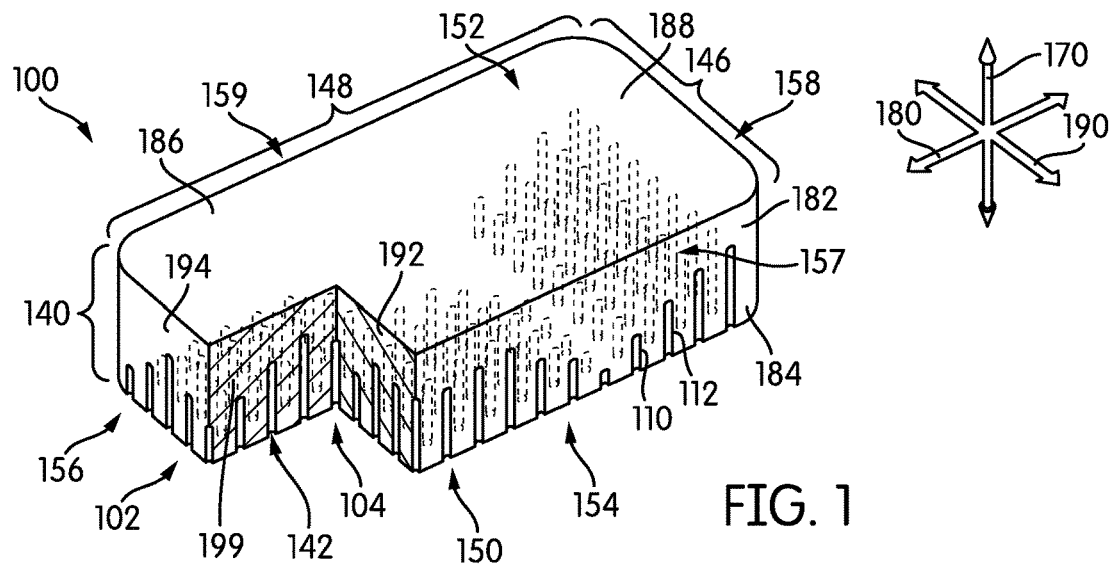
FIG. 1 is an isometric view of an embodiment of a cushioning element including apertures.
Figure 2:
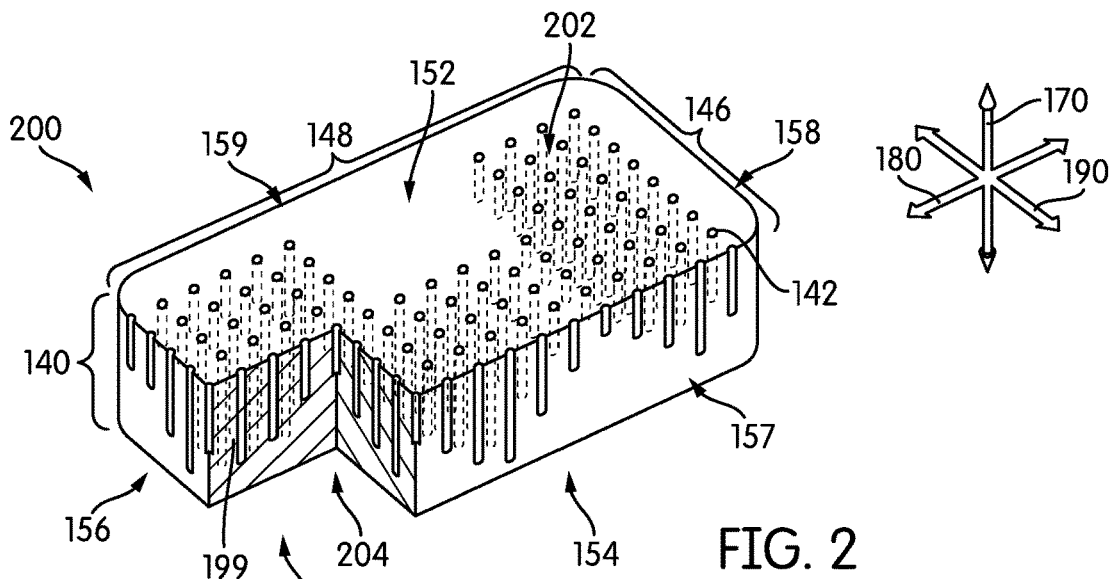
FIG. 2 is an isometric view of an embodiment of a cushioning element including apertures.
Figure 3:
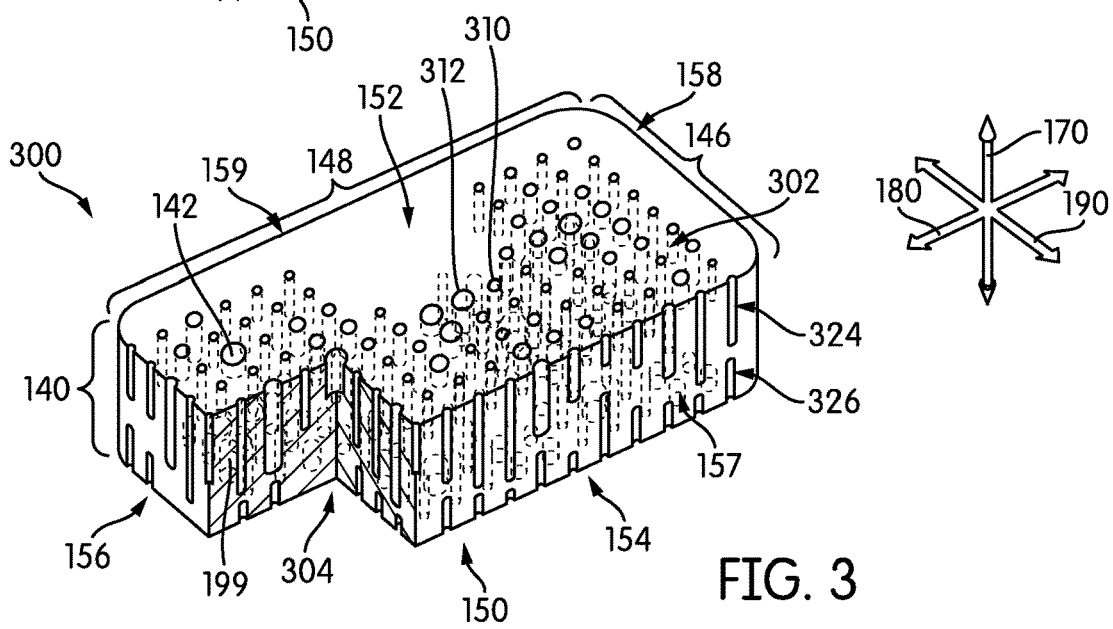
FIG. 3 is an isometric view of an embodiment of a cushioning element including apertures.

FIGS. 1-3 depict different embodiments of a portion of a cushioning element. A cushioning element can include provisions for increasing flexibility, fit, comfort, and/or stability during deformation or use of the cushioning element or article incorporating the cushioning element. Some of the embodiments of cushioning elements as disclosed herein may be utilized in various articles of apparel. In one embodiment, the cushioning elements may be used in an article of footwear. For example, as discussed in further detail below, in one embodiment, portions of a sole structure or sole member may incorporate or otherwise include a cushioning element.

For consistency and convenience, directional adjectives are also employed throughout this detailed description corresponding to the illustrated embodiments. The term "lateral" or "lateral direction" as used throughout this detailed description and in the claims refers to a direction extending along a width of a component or element. For example, a lateral direction may be oriented along a lateral axis 190 of a foot (see FIG. 20), which axis may extend between a medial side and a lateral side of the foot. Additionally, the term "longitudinal" or "longitudinal direction" as used throughout this detailed description and in the claims refers to a direction extending across a length of an element or component (such as a sole member). For example, a longitudinal direction may be oriented along a longitudinal axis 180, which axis may extend from a forefoot region to a heel region of a foot (see FIG. 20). It will be understood that each of these directional adjectives may also be applied to individual components of an article of footwear, such as an upper and/or a sole member. In addition, a vertical axis 170 refers to the axis perpendicular to a horizontal surface defined by longitudinal axis 180 and lateral axis 190.

FIG. 1 depicts an embodiment of a first cushioning element ("first element") 100, FIG. 2 depicts an embodiment of a second cushioning element ("second element") 200, and FIG. 3 depicts an embodiment of a third cushioning element ("third element") 300. As shown in FIGS. 1-3, in some embodiments, a cushioning element can include one or more apertures 150. For purposes of this description, apertures 150 are openings, apertures, holes, tunnels, or spaces that are disposed within the cushioning element. Generally, apertures 150 are initially formed along an exterior or outer surface of the cushioning element, and can extend any distance, and along any orientation, through an interior portion 199 (e.g., the thickness, breadth, or width) of the cushioning element. It should be understood that the terms exterior or outer surface with reference to a sole member does not necessarily indicate whether the sole member is actually exposed to the outer elements. Instead, outer surface or exterior surface refers to the outermost, outward-facing layer of the sole member. Interior portion 199 can be disposed between upper surface 152, lower surface 154, and a sidewall in some embodiments. Throughout the specification, it should be understood that characteristics being described as associated with a single aperture or aperture set can also characterize any other aperture or aperture set that may be referred to in the various embodiments.

The embodiments described herein may also include or refer to techniques, concepts, features, elements, methods, and/or components from: (a) U.S. patent application Ser. No. 14/722,758, filed May 27, 2015, titled "Article of Footwear Comprising a Sole Member with Apertures;" (b) U.S. patent application Ser. No. 14/722,782, filed May 27, 2015, titled "Article of Footwear Comprising a Sole Member with Aperture Patterns;" and (c) U.S. patent application Ser. No. 14/722,740, filed May 27, 2015, titled "Article of Footwear Comprising a Sole Member with Regional Patterns," the entirety of each application being herein incorporated by reference.

In different embodiments, cushioning elements may comprise any three-dimensional shape or geometry, including regular or irregular shapes. For example, cushioning elements may be substantially flat or narrow, and/or relatively thick or wide. The geometry and dimensions of a cushioning element can be configured for the application or exercise in which it will be used. For illustrative purposes, in FIGS. 1-3, the portions of cushioning elements have a generally oblong rectangular three-dimensional shape. Furthermore, for purposes of reference, as shown in FIGS. 1-3, each cushioning element may include upper surface 152 and lower surface 154 that is disposed opposite of upper surface 152. In some cases, upper surface 152 can be disposed adjacent to or joined to another component, such as an upper (see FIG. 26). In addition, in some cases, lower surface 154 can be a ground-contacting surface. However, in other cases, lower surface 154 may be disposed adjacent to another material (such as an outsole). The cushioning elements can further include additional exterior-facing surfaces. For example, as shown in FIGS. 1-3, the cushioning elements have four sidewalls, including first side 156, second side 157, third side 158, and fourth side 159. First side 156, second side 157, third side 158, and fourth side 159 may extend between upper surface 152 and lower surface 154. In addition, cushioning elements include thickness 140 extending between upper surface 152 and lower surface 154 along vertical axis 170, and width 146 extending from second side 157 to fourth side 159 along lateral axis 190, as well as length 148 extending along longitudinal axis 180 from first side 156 to third side 158. As noted in FIG. 1, thickness 140 may include upper portion 182 and lower portion 184. Width 146 may include forward portion 192 and rear portion 194. Furthermore, length 148 may include first side portion 186 and second side portion 188. Upper surface 152, lower surface 154, and sidewalls as depicted herein are associated with an outer surface of the cushioning elements.

It should be understood that other embodiments can have a fewer or greater number of exterior surfaces, and that the cushioning elements and the different regions of cushioning elements shown herein are for illustrative purposes only. In other embodiments, cushioning elements may include any contour, and may be any size, shape, thickness, or dimension, including regular and irregular shapes.

In some embodiments, apertures 150 have a rounded shape. In other embodiments, apertures 150 may include a wide variety of other geometries, including regular and irregular shapes. Apertures 150 may have a cross-sectional shape that is round, square, or triangular, for example. In some embodiments, apertures 150 may have a variety of geometric shapes that may be chosen to impart specific aesthetic or functional properties to a cushioning element. In one embodiment, apertures 150 may comprise a void that has a substantially cylindrical shape. In some embodiments, the cross-sectional diameter of the aperture may be substantially consistent or uniform throughout the length of the aperture.

In some cases, apertures 150 can be provided on or through lower surface 154 or upper surface 152 of the cushioning element. In other cases, apertures 150 can be provided on or through a side surface of the cushioning element. In one embodiment, apertures 150 can be provided on or through the side surfaces (for example, along first side 156, second side 157, third side 158, and/or fourth side 159) of the cushioning element as well as on lower surface 154 and upper surface 152 of the cushioning element.

In some embodiments, apertures 150 can provide means for decoupling or softening portions of a cushioning element in order to enhance its cushioning characteristics. For purposes of this disclosure, cushioning characteristics refer to the degree of fit, flexibility, cushioning, responsiveness, comfort, resilience, shock absorption, elasticity, and/or stability present in a portion of an element. For example, in some cases, apertures 150 can be formed in side portions and a lower portion of a cushioning element to reduce the cross-sectional profile of the element at particular regions and/or to facilitate increased flexibility between various portions of the element. In one embodiment, apertures 150 can be applied to side portions and an upper portion to form regions between adjacent portions of the element that articulate or bend with respect to one another.

Thus, in the present embodiments, the operation of the cushioning elements can involve providing a material variance in the element. The material variance can be accomplished by providing voids (apertures) that can comprise cut-outs through the cushioning element. As will be described below with respect to FIG. 25, the cut-outs can involve a removal of material from the element, thereby providing softer and/or cushioned regions in the portions that include the apertures.

Generally, apertures 150 can comprise various openings or holes arranged in a variety of orientations and in a variety of locations on or through the cushioning element. For example, as shown in FIG. 1, in some embodiments, a first aperture set 102 may include apertures 150 that extend in a direction generally aligned with vertical axis 170 through thickness 140 of first element 100. In first cutaway section 104 of first element 100 of FIG. 1, it can be seen that the apertures of first aperture set 102 begin along lower surface 154 and extend toward upper surface 152. Thus, apertures 150 of first aperture set 102 include a series of openings 142 (i.e., gaps or openings) along an exterior surface of first element 100. In FIG. 1, lower surface 154 comprises the exterior surface in which openings 142 (shown here as partially formed in first cutaway section 104) are formed. As will be discussed further below, apertures 150 may extend from an initial hole along an exterior surface to form apertures of varying sizes and lengths through thickness 140 of a cushioning element. Apertures 150 may be blind-hole apertures in some embodiments, where only one end of each aperture is open or exposed, while the opposite end of each aperture remains enclosed within the thickness of the element (i.e., only one end of each aperture may be exposed on an exterior surface of the element).

Furthermore, in FIG. 2, it can be seen that in another embodiment, there can be a second aperture set 202 comprising apertures 150 that extend in a direction generally aligned with vertical axis 170 through thickness 140 of second element 200. In second cutaway section 204 of second element 200 of FIG. 2, apertures of second aperture set 202 are formed along upper surface 152 and extend toward lower surface 154. In addition, in FIG. 2, openings 142 that comprise an exposed end of apertures 150 can be seen disposed along upper surface 152.

It should also be understood that in some embodiments of cushioning elements, there may be apertures 150 that are formed along multiple surfaces. For example, in FIG. 3, third aperture set 302 comprising apertures 150 that extend in a direction generally aligned with vertical axis 170 through thickness 140 of third element 300. However, in this embodiment, as shown in third cutaway section 304, third aperture set 302 includes apertures 150 with openings 142 formed along both lower surface 154 and upper surface 152. Thus, third aperture set 302 includes upper set 324 and lower set 326. Apertures 150 comprising upper set 324 extend from upper surface 152 toward lower surface 154, and apertures 150 comprising lower set 326 extend from lower surface 154 toward upper surface 152.

In different embodiments, the number of apertures 150 comprising each set of apertures can vary. For example, in one embodiment, first aperture set 102 can comprise between 1 and 100 apertures, or more than 100 apertures. In another embodiment, first aperture set 102 can comprise between 40 and 70 apertures. In still other embodiments, second aperture set 202 can include more than 100 apertures. In addition, in some embodiments, second aperture set 202 can include between 1 and 30 apertures. In other embodiments, second aperture set 202 can include more than 30 apertures. Similarly, in some embodiments, third aperture set 302 can include a wide range of numbers of apertures 150. Thus, depending on the cushioning characteristics desired, there can be more apertures or fewer apertures than illustrated in any set of apertures formed in a portion of a cushioning element.

As noted above, in some embodiments, apertures 150 may extend various distances through a cushioning element. For example, as shown in FIG. 1, some apertures 150 of first aperture set 102 may not extend above lower portion 184 of first element 100. However, other apertures 150 may extend further upward, above lower portion 184 and into upper portion 182. Likewise, in some cases, apertures 150 of second aperture set 202 may only be disposed in upper portion 182, while other apertures 150 may extend further downward. For example, an aperture may extend from upper surface 152, and be disposed at least partially within lower portion 184. It should be understood that the various portions can differ from that shown here and are for reference purposes only. Thus, apertures 150 can include any length from zero to nearly the entire length, width, or height of the cushioning element (including a diagonal length). In cases where the cushioning element varies in geometry from the generally oblong rectangular shape shown in FIGS. 1-3, apertures can be formed such that they extend up to the maximum length, thickness, breadth, or width associated with the cushioning element. Thus, in some embodiments, the length of each aperture can vary with the size or dimensions of the cushioning element.

Generally, the shape of one or more apertures 150 in a cushioning element can vary. In some cases, one or more apertures 150 may have a linear configuration or shape. In other cases, one or more apertures 150 may have a non-linear configuration or shape. In the embodiments of FIGS. 1-3, apertures 150 are shown having a generally linear shape, for example.

In different embodiments, the dimensions of one or more apertures 150 relative to one another can vary. For example, referring to FIG. 1, in some embodiments, the lengths of each aperture in first aperture set 102 can vary. For example, in one embodiment, apertures 150 of first aperture set 102 may be longer than other apertures 150 of first aperture set 102. Thus, in FIG. 1, a first aperture 110 has a smaller length than adjacent second aperture 112. In other cases, however, the lengths of each aperture in first aperture set 102 can vary in another manner. First aperture 110 may have a length that is substantially similar to or greater than the length of second aperture 112, for example. Thus, each aperture can have a length that differs from the length of other apertures, and apertures 150 located in different portions of a cushioning element can vary in length relative to one another. The length of an aperture can also vary with reference to longitudinal axis 180 and/or lateral axis 190. Some examples of this variety will be described further below.

Additionally, the size of each aperture can vary. For purposes of this description, the size of an aperture can refer to the cross-sectional diameter or size of an aperture. In some cases, the volume associated with the interior of an aperture can be correlated with the average cross-sectional diameter of the aperture. Referring to FIG. 3, in some cases, each aperture in third aperture set 302 can have a substantially similar size (e.g., cross-sectional diameter). In other cases, two or more apertures in third aperture set 302 can have substantially different sizes. For example, a third aperture 310 has a size that is smaller than the size of adjoining fourth aperture 312. In other cases, however, the sizes of each aperture in third aperture set 302 can vary in another manner. Third aperture 310 may have a size that is substantially similar to or greater than the size of fourth aperture 312, for example. Thus, each aperture can have a size that differs from the size of other apertures, and apertures 150 located in different portions of a cushioning element can vary in size relative to one another. In other cases, the size of each aperture can vary with the size of the cushioning element. It should be understood that the size of an aperture can vary throughout a single aperture, such that one region of an aperture is larger or smaller than another region of the same aperture. However, in other embodiments, the size of an aperture may remain substantially constant throughout the length of the aperture. Some examples of this variety will be described further below.

In some embodiments, apertures on different portions of a cushioning element can be generally parallel with one another with respect to another surface or side of the element. In some cases, apertures extending from the same surface of a cushioning element may be generally parallel with one another, such that they do not intersect. In other words, the apertures may be generally oriented in a similar direction. For example, apertures formed on lower surface 154 or upper surface 152 may be similarly oriented in a direction generally aligned with vertical axis 170. Thus, in different embodiments, apertures 150 may be associated with approximately similar longitudinal, lateral, or vertical orientations. In other embodiments, however, apertures on the side surfaces may not be parallel with one another. In one example, there may be apertures with openings 142 on first side 156 that are oriented in one direction, and apertures with openings 142 on first side 156 that are oriented along a different direction. Furthermore, it will be understood that in some embodiments, only some apertures may be generally aligned through upper portion 182, lower portion 184, first side portion 186, second side portion 188, forward portion 192, and/or rear portion 194, while other apertures disposed throughout the cushioning element may not be aligned. Therefore, it should be understood that while the embodiments of FIGS. 1-3 show apertures 150 having lengths extending along vertical axis 170, apertures can also be oriented so that they lie along any other direction (e.g., a horizontal, diagonal, or non-planar direction). For example, in some embodiments, apertures can form an angle less than 90 and greater than 0 degrees with respect to vertical axis 170, lateral axis 190, and/or longitudinal axis 180. In some cases, apertures can form an angle between 30 and 60 degrees with respect to vertical axis 170, lateral axis 190, and/or longitudinal axis 180.

As a result of the inclusion of different possible configurations of apertures 150, a cushioning element may have varying responsiveness to forces. In other words, apertures 150 can be disposed in a pattern that can help attenuate ground reaction forces and absorb energy, imparting different cushioning characteristics to the element. In the embodiments of FIGS. 4-9, a sequence of images representing possible responses of the cushioning elements under a load are shown.

Figure 4:
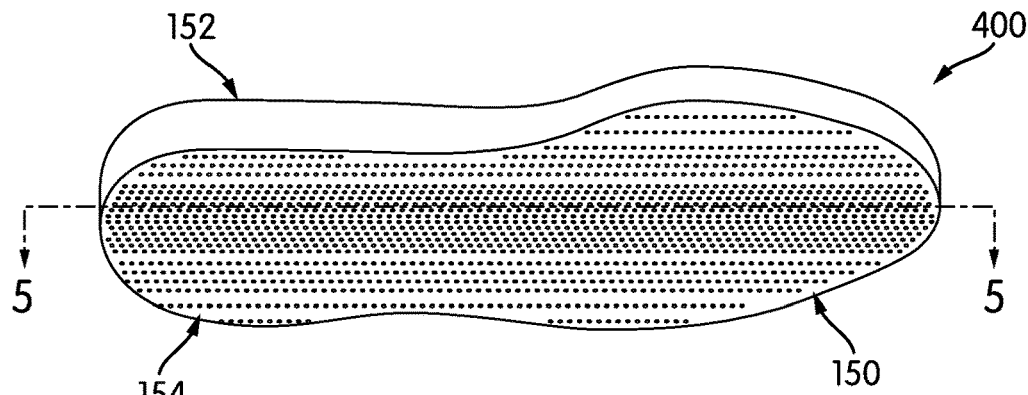
FIG. 4 is an isometric bottom view of an embodiment of a sole member comprising a cushioning element.
Figure 5:
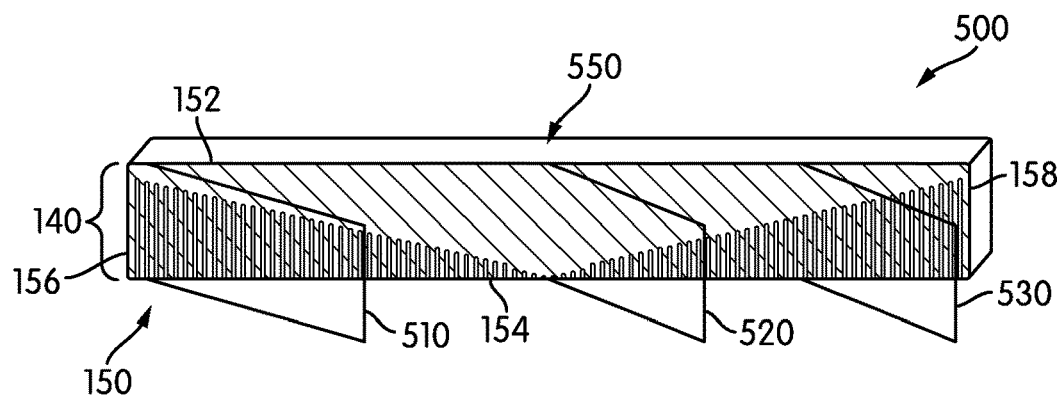
FIG. 5 is an isometric view of an embodiment of a cushioning element including apertures in an unloaded state.
Figure 6:
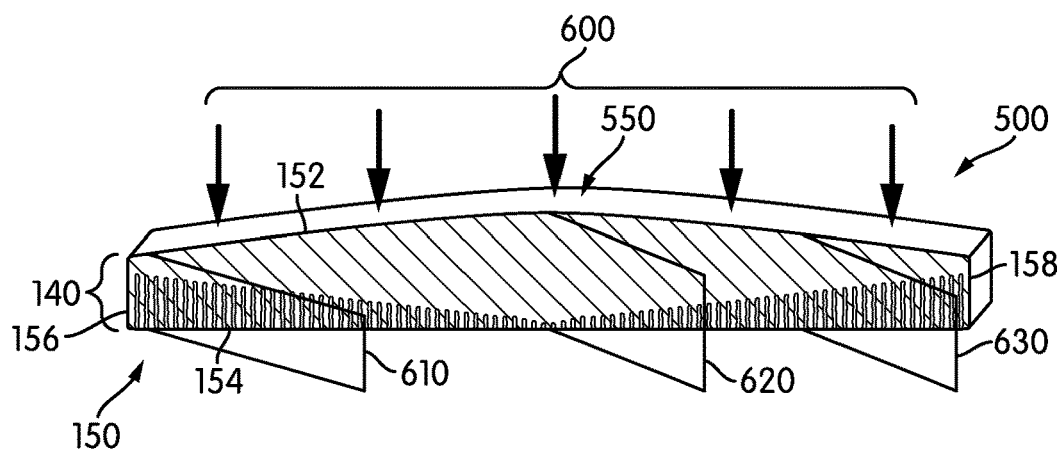
FIG. 6 is an isometric view of an embodiment of a cushioning element including apertures experiencing deformation.

For purposes of providing a contextual example to the reader, FIG. 4 depicts an embodiment of a first sole member 400. In FIG. 5, a cross section taken along the line 5-5 of FIG. 4 in first sole member 400 is shown, depicting fourth element 500. Fourth element 500 has a series of apertures 150 disposed along lower surface 154 and extending through thickness 140 at varying lengths. For example, apertures 150 disposed nearer to third side 158 are longer than apertures 150 disposed nearer to center 550 of fourth element 500. Furthermore, apertures 150 disposed nearer to center 550 of fourth element 500 are smaller than apertures 150 disposed closer to first side 156. In some embodiments, apertures 150 may form a geometric pattern. In other words, apertures 150 may be arranged such that there is a predictable rise and fall to the heights of the apertures throughout the cushioning element. In FIGS. 5-6, apertures 150 decrease in length as they approach center 550 of fourth element 500, and then increase in length as they move further away from center 550. A regular arrangement as shown in fourth element 500 may provide more consistent cushioning for a user in some cases. However, it should be understood that, in other embodiments, apertures 150 may have a random height arrangement.

For purposes of convenience, heights can be associated with different portions of fourth element 500. In FIG. 5, a first height 510, a second height 520, and a third height 530 are identified. First height 510 is associated with the portion of fourth element 500 toward first side 156, second height 520 is associated with the portion of fourth element 500 toward center 550, and third height 530 is associated with the portion of fourth element 500 toward third side 158. In FIG. 5, first height 510, second height 520, and third height 530 are substantially similar, such that thickness 140 is generally uniform through fourth element 500.

When fourth element 500 undergoes first load 600 (represented by arrows), as shown in FIG. 6, the arrangement of apertures 150 can alter the cushioning responsiveness of the material. In FIG. 6, first load 600 is directed downward in a direction generally aligned with vertical axis 170 and distributed in a substantially constant or uniform manner over upper surface 152 of fourth element 500. As fourth element 500 experiences the force of first load 600, fourth element 500 can deform.

In some embodiments, when cushioning elements are compressed, they can deform in different ways. The deformation that occurs can be related to the location of any apertures, and/or the size and orientation of the apertures. Thus, apertures 150 may function together within the material of the cushioning element to provide variations in the relative stiffness, degree of ground reaction force attenuation, and energy absorption properties of the cushioning element. These cushioning characteristics may be altered to meet the specific demands of the activity for which the cushioning element is intended to be used, through the methods described herein.

In some embodiments, when the compressive force of first load 600 is applied to fourth element 500, for example, the areas that include more apertures and/or apertures of greater size or length may deform to a greater extent than the portions of fourth element 500 that have fewer apertures and/or apertures of smaller size or length. As a result of the application of first load 600, the aperture openings can be compressed and/or deformed, as shown in FIG. 6. In the region nearest to third side 158, where there are longer apertures relative to the center of fourth element 500, the deformation is greater. Similarly, in the region nearest to first side 156, where the apertures are longer relative to the apertures disposed proximate center 550, the degree of deformation is greater. Thus, the least deformation of fourth element 500 occurs near center 550, where there are shorter or smaller apertures.

In some embodiments, the deformation that occurs throughout fourth element 500 can be measurable in part by the changed shape and height of fourth element 500 and/or the changed shape and heights of apertures 150. Specifically, in FIG. 6, fourth height 610, fifth height 620, and sixth height 630 are identified. Fourth height 610 is associated with the portion of fourth element 500 toward first side 156, fifth height 620 is associated with the portion of fourth element 500 toward center 550 of fourth element 500, and sixth height 630 is associated with the portion of fourth element 500 toward third side 158. Referring to FIGS. 5 and 6, as a result of first load 600, it can be seen that fourth height 610 is less than first height 510, fifth height 620 is less than second height 520, and sixth height 630 is less than third height 530. Furthermore, in FIG. 6, fourth height 610, fifth height 620, and sixth height 630 are substantially different from one another, such that thickness 140 is generally non-uniform through fourth element 500. In other words, various contours have been formed along upper surface 152 where first load 600 has been applied. The contours may vary in a manner generally corresponding to the arrangement of apertures 150 disposed in fourth element 500 in some embodiments. Thus, fifth height 620 is greater than both fourth height 610 and sixth height 630, and sixth height 630 is greater than fourth height 610.

In some embodiments, the shape or orientation of the apertures may also change as a result of an applied force. Depending on the magnitude and the direction of the force (s) applied, the changes in area or shape may vary. For example, referring to FIG. 6, in one embodiment, fourth element 500 may be exposed to a force or load whereby apertures become deformed not only by becoming more compact, but also by curling or otherwise becoming increasingly non-linear and/or irregular. In one embodiment, the area or volume of an aperture may decrease when a compressive force is applied.

Figure 7:
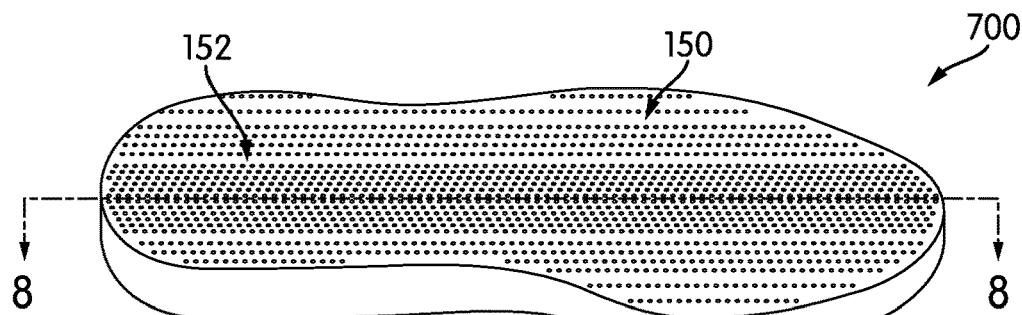
FIG. 7 is an isometric bottom view of an embodiment of a sole member comprising a cushioning element.
Figure 8:
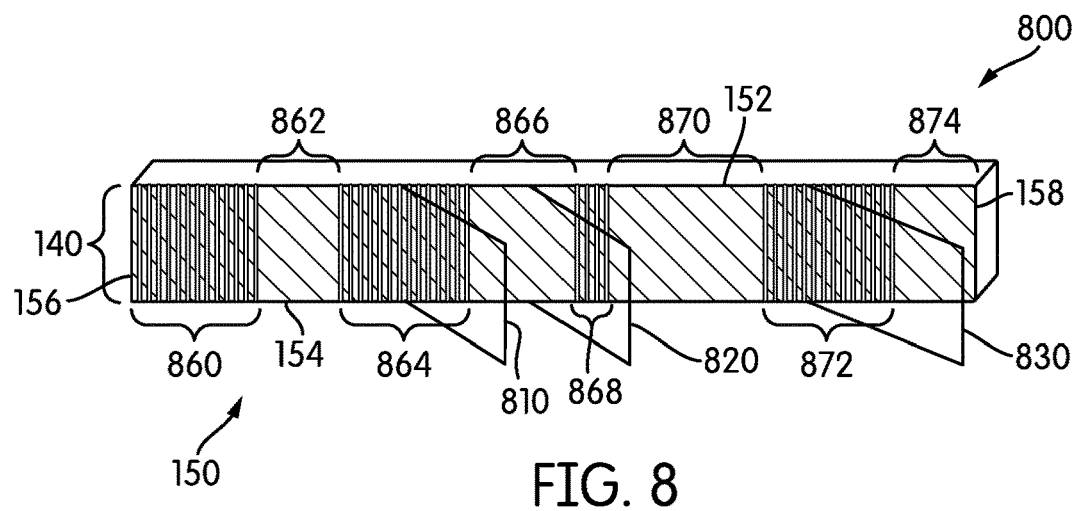
FIG. 8 is an isometric view of an embodiment of a cushioning element including apertures in an unloaded state.
Figure 9:
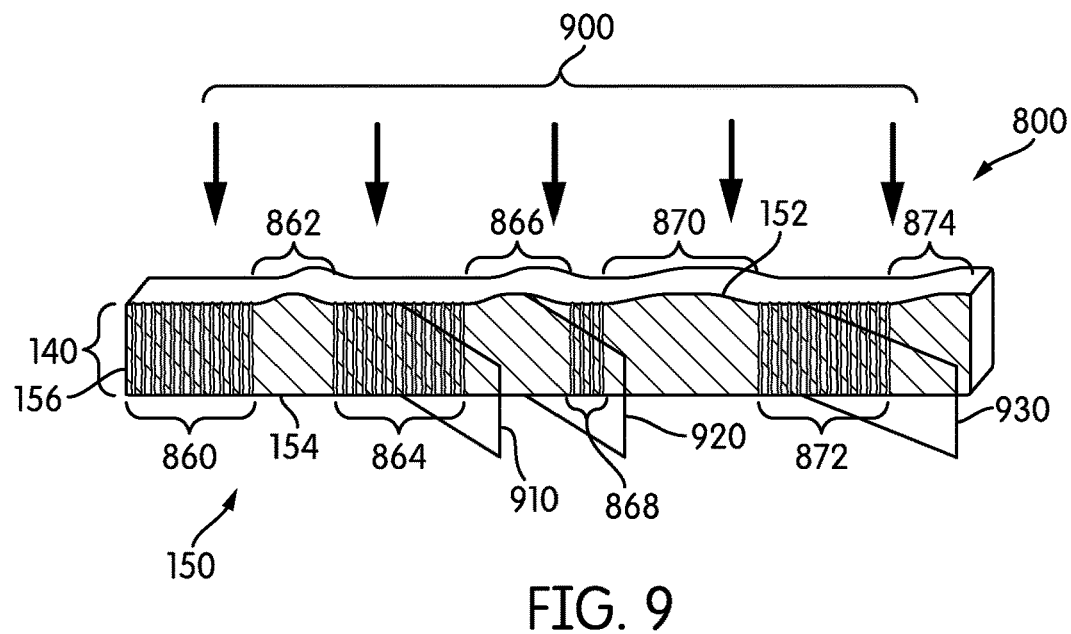
FIG. 9 is an isometric view of an embodiment of a cushioning element including apertures experiencing deformation.

Similarly, compressive forces can produce responses in other types of cushioning elements. For purposes of providing a contextual example to the reader, FIG. 7 depicts an embodiment of second sole member 700. In FIG. 8, a cross-section taken along the line 8-8 of FIG. 7 in second sole member 700 depicts an unloaded fifth cushioning element ("fifth element") 800. Fifth element 800 has a series of through-hole apertures 150 extending from lower surface 154, through thickness 140, to upper surface 152. As noted above, in some embodiments, apertures 150 may be disposed along only some areas of fifth element 800. In FIGS. 8 and 9, fifth element 800 includes first region 860, second region 862, third region 864, fourth region 866, fifth region 868, sixth region 870, seventh region 872, and eighth region 874. First region 860, third region 864, fifth region 868, and seventh region 872 comprise portions that include apertures 150, while second region 862, fourth region 866, sixth region 870, and eighth region 874 comprise portions that do not include apertures 150.

When second sole member 700 and/or fifth element 800 undergo second load 900 (represented by arrows), as shown in FIG. 9, the arrangement of apertures 150 can alter the cushioning responsiveness of the material. In FIG. 9, second load 900 is directed downward in a direction generally aligned with vertical axis 170 and distributed in a substantially constant manner over upper surface 152 of fifth element 800. Similar to fourth element 500 described with respect to FIGS. 5-6, as fifth element 800 experiences the force of second load 900, fifth element 800 can deform. The deformation that occurs can be related to the location of any aperture, and/or the size and orientation of the apertures in some embodiments.

When the compressive force of second load 900 is applied to fifth element 800, for example, the areas that include more apertures and/or apertures of greater size may deform to a greater extent than the portions of fifth element 800 that have fewer apertures and/or apertures of smaller size. Thus, as a result of the application of second load 900, any aperture openings or passageways can be compressed and/or deformed. In some embodiments, in regions with apertures, the cushioning response can be greater relative to the regions without apertures.

For purposes of convenience, heights are associated with different portions of fifth element 800. For example, referring to FIG. 8, seventh height 810 is associated with third region 864, eighth height 820 is associated with fourth region 866, and ninth height 830 is associated with seventh region 872. It can be seen that in the unloaded configuration of FIG. 8, seventh height 810, eighth height 820, and ninth height 830 are substantially similar, such that thickness 140 is generally uniform through fifth element 800.

However, when fifth element 800 undergoes second load 900 (represented by arrows), as shown in FIG. 9, the arrangement of apertures 150 can alter the responsiveness of the material. In FIG. 9, tenth height 910 associated with third region 864, eleventh height 920 associated with fourth region 866, and twelfth height 930 associated with seventh region 872 can be identified.

Referring to FIGS. 8 and 9, in response to second load 900, the overall height of fifth element 800 is lessened. For example, tenth height 910 is less than seventh height 810, eleventh height 920 is less than eighth height 820, and twelfth height 930 is less than ninth height 830. Comparing FIG. 8 with FIG. 9, it can be seen that in the regions where there are no apertures, the degree of deformation is substantially less. For example, while the entire surface of fifth element 800 is compressed and the overall height of the cushioning element decreases, various contours can be formed along upper surface 152 where second load 900 has been applied. It can be seen that tenth height 910 differs substantially from eleventh height 920, and eleventh height 920 differs from twelfth height 930, such that thickness 140 is generally non-uniform throughout fifth element 800. In some embodiments, these contours may vary in a manner generally corresponding to the arrangement of apertures 150 disposed in fifth element 800. Thus, eleventh height 920, which is associated with an area that does not include apertures, is greater than tenth height 910 and twelfth height 930, which include apertures. This allows each area to provide different cushioning properties.

Thus, exposure to various forces may also produce a change in the shape or geometry, size, and/or height of cushioning elements and the apertures that may be disposed within the cushioning element. It should be understood that while first load 600 and second load 900 are shown as being generally uniform, other loads may be non-uniform. Depending on the magnitude and the direction of the force (s) applied, changes in area, volume, dimensions, and/or shape of the cushioning element may vary. In some embodiments, a different force may permit the cushioning element to expand in a lateral or longitudinal direction, such that the overall length of the element increases. In other embodiments, different forces may alter the responses of the cushioning element.

It should be noted that the various degrees of deformation described and shown here are for purposes of illustration. In some situations, the cushioning element may not undergo compression to the extent depicted, or may deform more or less, depending on various factors such as the materials used in the production of the cushioning element, as well as its incorporation in other objects or articles. For example, if a cushioning element is joined or attached to a less reactive material, the compressive and/or expansive properties described herein may differ, or be limited. In some embodiments, when the cushioning element is joined to a strobel or other structure, the capacity of expansion may decrease. In some embodiments, the perimeter of the cushioning element may be fixed, e.g., bonded to a strobel layer or another sole layer. However, in such embodiments, the cushioning characteristics of the cushioning element may still facilitate increased flexibility and cushioning.

Furthermore, it should be understood that while fourth element 500 and fifth element 800 may experience various forces and deformation, the deformation may be elastic. In other words, once the load is removed or decreased, the cushioning element may recover and return to its original dimensions and/or shape, or to dimensions and/or a shape substantially similar to the original, unloaded configuration.

It should be understood that, in some embodiments, the shape or orientation of the apertures may also change. Depending on the magnitude and the direction of the force (s) applied, the changes in area or shape may vary. For example, in one embodiment, fourth element 500 and/or fifth element 800 may be exposed to a force or load whereby apertures become deformed not only by becoming more compact, but also by curling or otherwise becoming increasingly non-linear and/or irregular. In one embodiment, the area or volume of an aperture may increase when a compressive force is applied.

Referring to FIGS. 10-19, in different embodiments, a specific pattern may be selected and/or formed in the cushioning elements. In some embodiments, the cushioning characteristics of a cushioning element may be modified by removing material and/or drilling apertures in the cushioning element to form a specific pattern. In some embodiments, a plurality of apertures may be disposed in a regular or irregular pattern along a portion of a cushioning element. In some cases, the apertures can be disposed in regular intervals. For purposes of this disclosure, a regular pattern refers to a consistent (or otherwise generally unvarying), repeating, geometric, periodic, steady, and/or reoccurring arrangement. For example, a plurality of openings or apertures that are disposed in a circular, ring, or other geometric shape may be regularly arranged.

In some embodiments, apertures can be disposed along a common circumference, or extend along a common radius, to form a regular pattern. Apertures located along or associated with the same circumference can be understood to mean that the apertures are disposed at a substantially similar radial distance from a center point. For purposes of this disclosure, apertures disposed on a common or the same circumference may also be understood to describe apertures that are disposed in a manner that form a generally round or curved perimeter or boundary. The "circumference" can be continuous or discontinuous in different embodiments. In other words, the boundary of a circumference can be continuous (i.e., a solid or unbroken boundary or shape), or discontinuous (i.e., a general boundary or shape that is broken, such that the shape is implied by the arrangement of the apertures, and can be dotted, or include spaces or openings along the perimeter of the shape).

Figure 10:
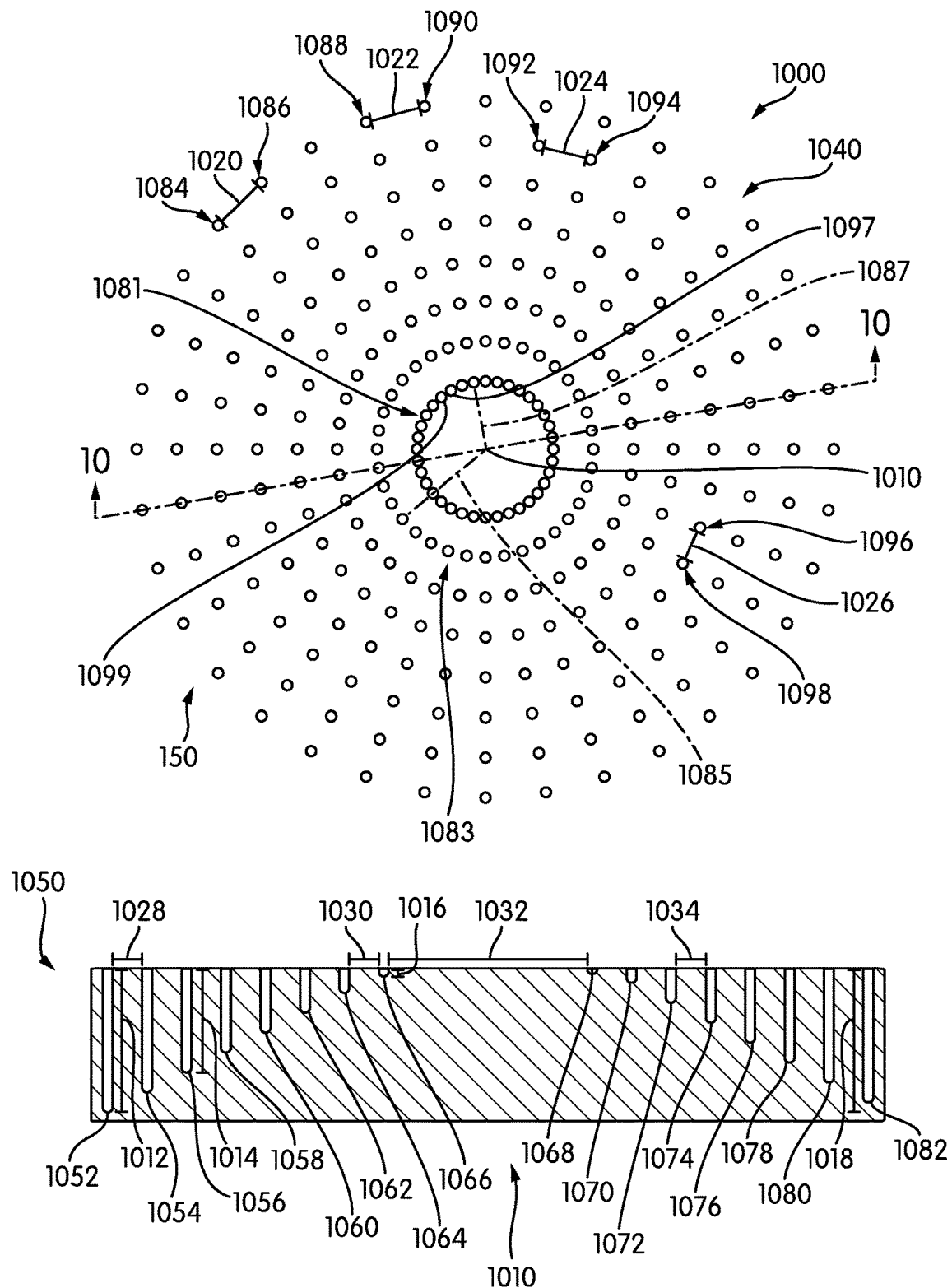
FIG. 10 is an isometric view of an embodiment of an aperture pattern.

A few examples of regular patterns that may be formed in a cushioning element are depicted in FIGS. 10-13. It should be understood that these patterns are for illustrative purposes only, and any other aperture pattern may be formed using the principles disclosed herein. In FIG. 10, a regular first pattern ("first pattern") 1000 is shown. First pattern 1000 has a generally round configuration, comprising a series of apertures 150 disposed in a repeated circular arrangement. In other words, there are multiple circumferences (of apertures) of different sizes in first pattern 1000. In other embodiments, a first pattern may refer to a single circumference within a larger aperture pattern.

As noted above, it should be understood that the pattern depicted in first pattern 1000 may include apertures 150 of various shapes and/or dimensions. Thus, apertures 150 may be round or another regular or irregular shape. Furthermore, apertures 150 may comprise different lengths. For example, 16 apertures are depicted in cross-sectional view 1050 of first pattern 1000 taken across the line 10-10. In cross-sectional view 1050, a first aperture 1052, a second aperture 1054, a third aperture 1056, a fourth aperture 1058, a fifth aperture 1060, a sixth aperture 1062, a seventh aperture 1064, an eighth aperture 1066, a ninth aperture 1068, a tenth aperture 1070, an eleventh aperture 1072, a twelfth aperture 1074, a thirteenth aperture 1076, a fourteenth aperture 1078, a fifteenth aperture 1080, and a sixteenth aperture 1082 are shown. It should be understood that in other embodiments there may be a greater or lesser number of apertures included in first pattern 1000 than shown here.

In some embodiments, each aperture may have a length that differs from that of an adjacent aperture, or one or more apertures may have a substantially similar length. In some cases, apertures 150 may have an oscillating or tapering pattern of lengths. For example, in cross-sectional view 1050 of FIG. 10 it can be seen that apertures 150 decrease in length as they approach a center 1010 (i.e., in a radially inward direction), and then increase in length again as they move away from center 1010 (i.e., move in a radially outward direction). For purposes of this disclosure, center 1010 may refer to the approximate origin of the circumference of apertures depicted. As an illustration, in some cases, first aperture 1052 can have a first length 1012, third aperture 1056 can have a second length 1014, eighth aperture 1066 can have a third length 1016, and sixteenth aperture 1082 can have a fourth length 1018. In some embodiments, first length 1012 may be greater than second length 1014. In some embodiments, second length 1014 may be greater than third length 1016. Furthermore, third length 1016 and/or second length 1014 may be smaller than fourth length 1018. In some cases, different apertures can have similar lengths. In one embodiment, first length 1012 may be substantially similar to fourth length 1018.

In different embodiments, a "mirrored" pattern may be formed. In one embodiment, apertures disposed along the same circumference can have substantially similar lengths. In other words, apertures disposed along the same circumference may be substantially similar in length to one another. Thus, in one case, fifth aperture 1060 and twelfth aperture 1074, being disposed on the same circumference, may comprise similar lengths. In some embodiments, two or more apertures disposed along a common circumference may have similar lengths. However, in other embodiments, the lengths of apertures may differ from that shown here, may have a different repeated pattern, or may be random.

In addition, referring to FIG. 10, it can be seen that each aperture may be disposed at a distance from its neighboring aperture. In different embodiments, the distances between apertures may be similar or they may vary. In one embodiment, the distance between two apertures may vary based on whether the two apertures are disposed along a common circumference (i.e., are disposed at a similar radial distance from center 1010), or whether they are disposed along different circumferences.

As shown in FIG. 10, in some cases, there may be two or more apertures disposed adjacent to one another, but disposed on different circumferences. In cross-sectional view 1050, it can be seen that first aperture 1052 is spaced at a first radial distance 1028 from second aperture 1054, and seventh aperture 1064 is spaced at a second radial distance 1030 from eighth aperture 1066. In addition, eighth aperture 1066 is spaced at a third radial distance 1032 from ninth aperture 1068, and eleventh aperture 1072 is spaced at a fourth radial distance 1034 from twelfth aperture 1074. In some embodiments, first radial distance 1028 can be similar to or different from second radial distance 1030. In FIG. 10, first radial distance 1028 is substantially similar to both second radial distance 1030 and fourth radial distance 1034. In other words, apertures adjacent to one another and disposed along neighboring circumferences may be spaced apart from one another at generally uniform distances.

However, in some embodiments, there may be a greater or lesser distance between apertures disposed on different circumferences. In some cases, some apertures can be spaced apart at irregular distances from one another. In one example, third radial distance 1032 can be greater than first radial distance 1028, second radial distance 1030, and/or fourth radial distance 1034. In one embodiment, third radial distance 1032 may represent the diameter of the circumference in which eighth aperture 1066 and ninth aperture 1068 are arranged. In some embodiments, third radial distance 1032 may be approximately twice as large as first radial distance 1028. In other embodiments, third radial distance 1032 may be more than twice as great as first radial distance 1028. In other words, a portion of a cushioning element disposed proximate to center 1010 may not include apertures. In one embodiment, the distance between eighth aperture 1066 and ninth aperture 1068 may be a reflection of the lack of additional circumferentially disposed apertures near center 1010.

Similarly, in different embodiments, apertures that are disposed adjacent to one another and that share a common circumference can be spaced apart at regular or similar intervals. For example, in FIG. 10, a seventeenth aperture 1084 and an eighteenth aperture 1086 are separated by a first circumferential distance 1020, and a nineteenth aperture 1088 and a twentieth aperture 1090 are separated by a second circumferential distance 1022. In some embodiments, first circumferential distance 1020 and second circumferential distance 1022 may be substantially similar or they may differ. In FIG. 10, first circumferential distance 1020 and second circumferential distance 1022 are substantially similar. Thus, in some embodiments, apertures disposed along a common circumference may be spaced uniformly apart from one another.

Furthermore, the distance between neighboring apertures disposed along a first circumference can differ or be similar to the distance between neighboring apertures disposed along a second circumference. For example, a twenty-first aperture 1092 and a twenty-second aperture 1094 disposed on a common first circumference can be separated by a third circumferential distance 1024, and a twenty-third aperture 1096 and a twenty-fourth aperture 1098 disposed on a common second circumference are separated by a fourth circumferential distance 1026. In some embodiments, third circumferential distance 1024 and fourth circumferential distance 1026 can be similar. In other embodiments, third circumferential distance 1024 and fourth circumferential distance 1026 can differ. In FIG. 10, third circumferential distance 1024 is greater than fourth circumferential distance 1026.

It may also be understood that, in some cases, a circumferential distance may be close to zero or be approximately zero such that two apertures are touching or merged. For example, a twenty-fifth aperture 1097 and twenty-sixth aperture 1099 on the circumference nearest center 1010 are shown to be nearly touching one another. In other embodiments, two apertures may be disposed close enough to one another so as to form a substantially continuous opening similar to a siping. This feature will be discussed further with respect to FIGS. 11 and 12.

In some cases, a pattern can be formed whereby the distances between apertures disposed along a common circumference may decrease or increase along a direction. For example, in first pattern 1000, apertures that are disposed further radially outward from center 1010 are spaced apart at larger distances, while apertures that are disposed further radially inward toward center 1010 are spaced from one another at relatively closer distances. For example, in the direction extending from an outermost perimeter 1040 to center 1010, the distance between apertures can decrease or increase. Thus, in one embodiment, first circumferential distance 1020 may be greater than third circumferential distance 1024, and third circumferential distance 1024 may be greater than fourth circumferential distance 1026.

Figure 11:
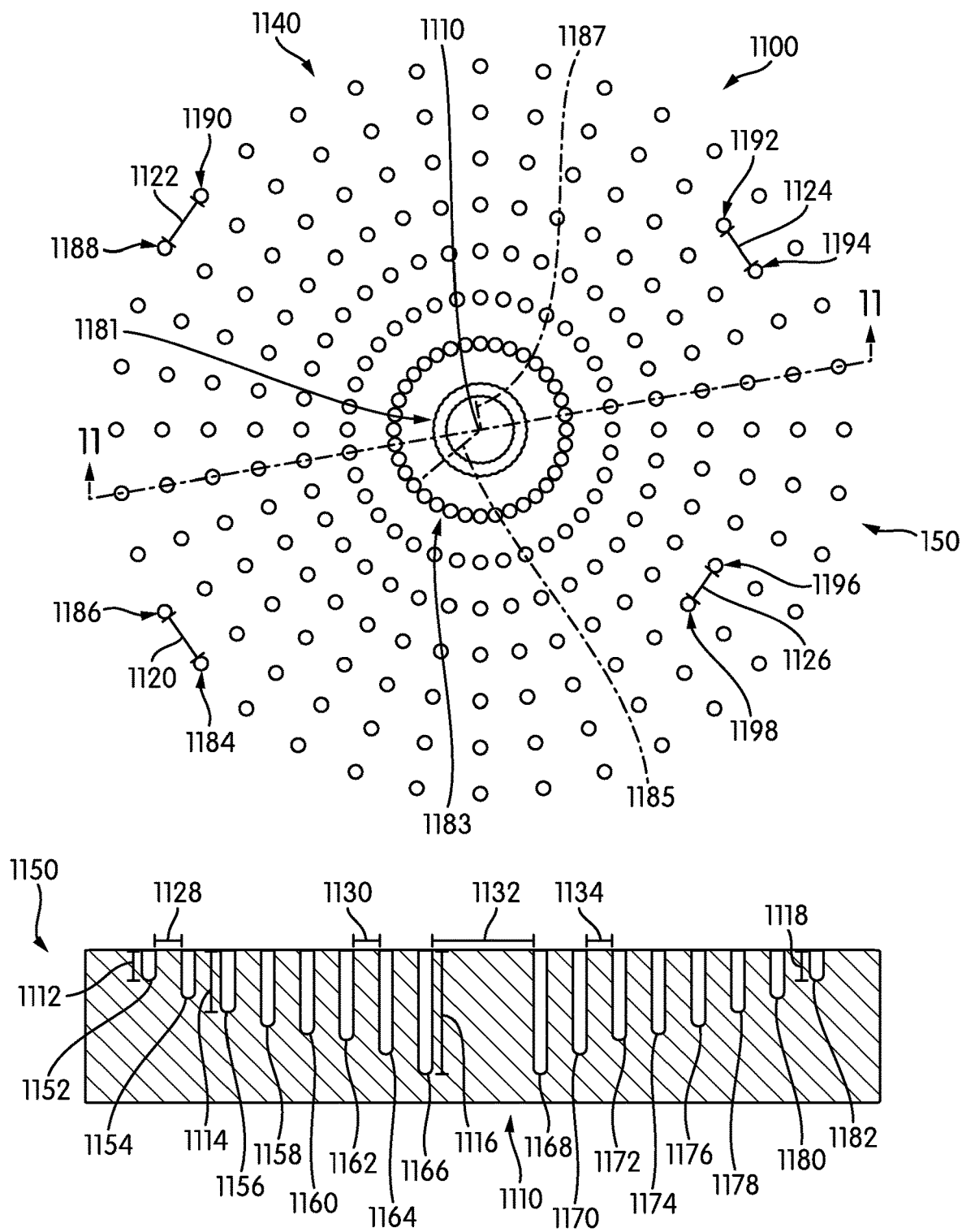
FIG. 11 is an isometric view of an embodiment of an aperture pattern.

In FIG. 11, a regular second pattern ("second pattern") 1100 is shown. Similar to first pattern 1000 of FIG. 10, second pattern 1100 has a generally round configuration, comprising a series of apertures 150 disposed in a repeated circular arrangement. As noted above, it should be understood that the pattern depicted in second pattern 1100 may include apertures 150 of various shapes and/or dimensions. Thus, apertures 150 may be round or another regular or irregular shape.

Furthermore, apertures 150 may comprise different or similar lengths. For example, 16 apertures are depicted in a cross-sectional view 1150 of second pattern 1100, taken across the line 11-11. In cross-sectional view 1150, a first aperture 1152, a second aperture 1154, a third aperture 1156, a fourth aperture 1158, a fifth aperture 1160, a sixth aperture 1162, a seventh aperture 1164, an eighth aperture 1166, a ninth aperture 1168, a tenth aperture 1170, an eleventh aperture 1172, a twelfth aperture 1174, a thirteenth aperture 1176, a fourteenth aperture 1178, a fifteenth aperture 1180, and a sixteenth aperture 1182 are shown. It should be understood that in other embodiments there may be a greater or lesser number of apertures included in second pattern 1100 than shown here.

In some embodiments, each aperture may have a length that differs from that of an adjacent aperture, or one or more apertures may have a substantially similar length. In some cases, apertures 150 may have an oscillating or tapering pattern of lengths. For example, in cross-sectional view 1150 of FIG. 11, it can be seen that apertures 150 increase in length as they approach a center 1110 (i.e., in a radially inward direction), and then decrease in length again as they move away from center 1110 (i.e., radially outward). For purposes of this disclosure, center 1110 may refer to the approximate origin of the circumference of apertures depicted. As an illustration, in some cases, first aperture 1152 can have a first length 1112, third aperture 1156 can have a second length 1114, eighth aperture 1166 can have a third length 1116, and sixteenth aperture 1182 can have a fourth length 1118. In some embodiments, first length 1112 may be smaller than second length 1114. In some embodiments, second length 1114 may be smaller than third length 1116. Furthermore, third length 1116 and/or second length 1114 may be greater than fourth length 1118. In some cases, different apertures can have similar lengths. In one embodiment, first length 1112 may be substantially similar to fourth length 1118.

In different embodiments, similar to FIG. 10, a "mirrored" pattern may be formed. In one embodiment, apertures disposed along the same circumference can have substantially similar lengths. In other words, apertures disposed along the same circumference may be substantially similar in length to one another. Thus, in one case, fifth aperture 1160 and twelfth aperture 1174 may have similar lengths. In some embodiments, two or more apertures disposed along a common circumference may have similar lengths. However, in other embodiments, the lengths of apertures may differ from that shown here, may have a different repeated pattern, or may be random.

In addition, referring to FIG. 11, it can be seen that each aperture can be disposed at a distance from its neighboring aperture. In some embodiments, the distances between apertures 150 may be similar or they may vary. The distances between two apertures may be varied based on whether the two apertures are disposed along a common circumference (i.e., are disposed at a similar radial distance from center 1110), or whether they are disposed along different circumferences.

As shown in FIG. 11, in some cases, there may be two or more apertures disposed adjacent to one another, yet disposed on different circumferences. In cross-sectional view 1150, it can be seen that first aperture 1152 is spaced at a first radial distance 1128 from second aperture 1154, while seventh aperture 1164 is spaced at a second radial distance 1130 from eighth aperture 1166. In addition, eighth aperture 1166 is spaced at a third radial distance 1132 from ninth aperture 1168, and tenth aperture 1170 is spaced at a fourth radial distance 1134 from eleventh aperture 1172. In some embodiments, first radial distance 1128 can be similar to or differ from second radial distance 1130. In FIG. 11, first radial distance 1128 is substantially similar to both second radial distance 1130 and fourth radial distance 1134. In other words, apertures arranged along neighboring circumferences may be spaced apart at generally uniform distances.

However, in some embodiments, there may be a greater or lesser distance between apertures disposed on different circumferences. In some cases, such apertures can be spaced apart at irregular distances from one another. In one example, third radial distance 1132 can be greater than first radial distance 1128, second radial distance 1130, and/or fourth radial distance 1134. In one embodiment, third radial distance 1132 may represent the diameter of the circumference in which eighth aperture 1166 and ninth aperture 1168 are arranged. In one embodiment, third radial distance 1132 may be approximately twice as large as first radial distance 1128. In other embodiments, third radial distance 1132 may be more than twice as great as first radial distance 1128. In other words, a portion of a cushioning element disposed proximate to center 1110 may not include apertures. In one embodiment, the distance between eighth aperture 1166 and ninth aperture 1168 may be larger, reflecting a lack of additional apertures disposed toward center 1110.

Furthermore, in different embodiments, apertures disposed adjacent to one another and that share a common circumference can be spaced apart at regular or similar intervals. For example, in FIG. 11, a seventeenth aperture 1184 and an eighteenth aperture 1186 are separated by a first circumferential distance 1120, and a nineteenth aperture 1188 and a twentieth aperture 1190 are separated by a second circumferential distance 1122. In some embodiments, first circumferential distance 1120 and second circumferential distance 1122 may be substantially similar or they may differ. In FIG. 11, first circumferential distance 1120 and second circumferential distance 1122 are substantially similar. Thus, in some embodiments, apertures disposed along a common circumference may be spaced uniformly apart from one another.

In addition, the distance between neighboring apertures disposed along a first circumference can differ or be similar to the distance between neighboring apertures disposed along a second circumference. For example, a twenty-first aperture 1192 and a twenty-second aperture 1194 disposed on a common first circumference can be separated by a third circumferential distance 1124, and a twenty-third aperture 1196 and a twenty-fourth aperture 1198 disposed on a common second circumference are separated by a fourth circumferential distance 1126. In some embodiments, third circumferential distance 1124 and fourth circumferential distance 1126 can be similar. In other embodiments, third circumferential distance 1124 and fourth circumferential distance 1126 can differ. In FIG. 11, third circumferential distance 1124 is greater than fourth circumferential distance 1126.

As noted above, in some embodiments, a circumferential distance between two apertures may be close to zero or be approximately zero. In other words, two apertures can approach, touch, and/or merge with one another. For example, an innermost circumference comprising a first circumference 1181 includes a series of apertures whose edges are touching one another. In other words, each aperture of first circumference 1181 is disposed close enough to one another so as to form a substantially continuous opening similar to a siping. In different embodiments, this siping facsimile can be a result of the varying degrees of merging between adjoining apertures. In some embodiments, apertures may be formed in various portions of a cushioning element to create a siping-like region, groove, or channel, through the cushioning element. While the arrangement can provide variations in cushioning, there may be other benefits, including enhanced traction or grip of the exterior surface. Various designs or flexible regions may also be formed by the inclusion of such siped apertures.

Furthermore, in some embodiments, a pattern can be formed whereby the distances between apertures disposed along a common circumference may decrease or increase along a direction. For example, in second pattern 1100, apertures that are disposed further radially outward are spaced apart at larger distances, while apertures that are disposed further radially inward are spaced apart at closer distances. For example, in the direction extending from an outermost perimeter 1140 to center 1110, the distance between apertures can decrease or increase. Thus, in one embodiment, first circumferential distance 1120 may be greater than third circumferential distance 1124, and third circumferential distance 1124 may be greater than fourth circumferential distance 1126.

Figure 12:
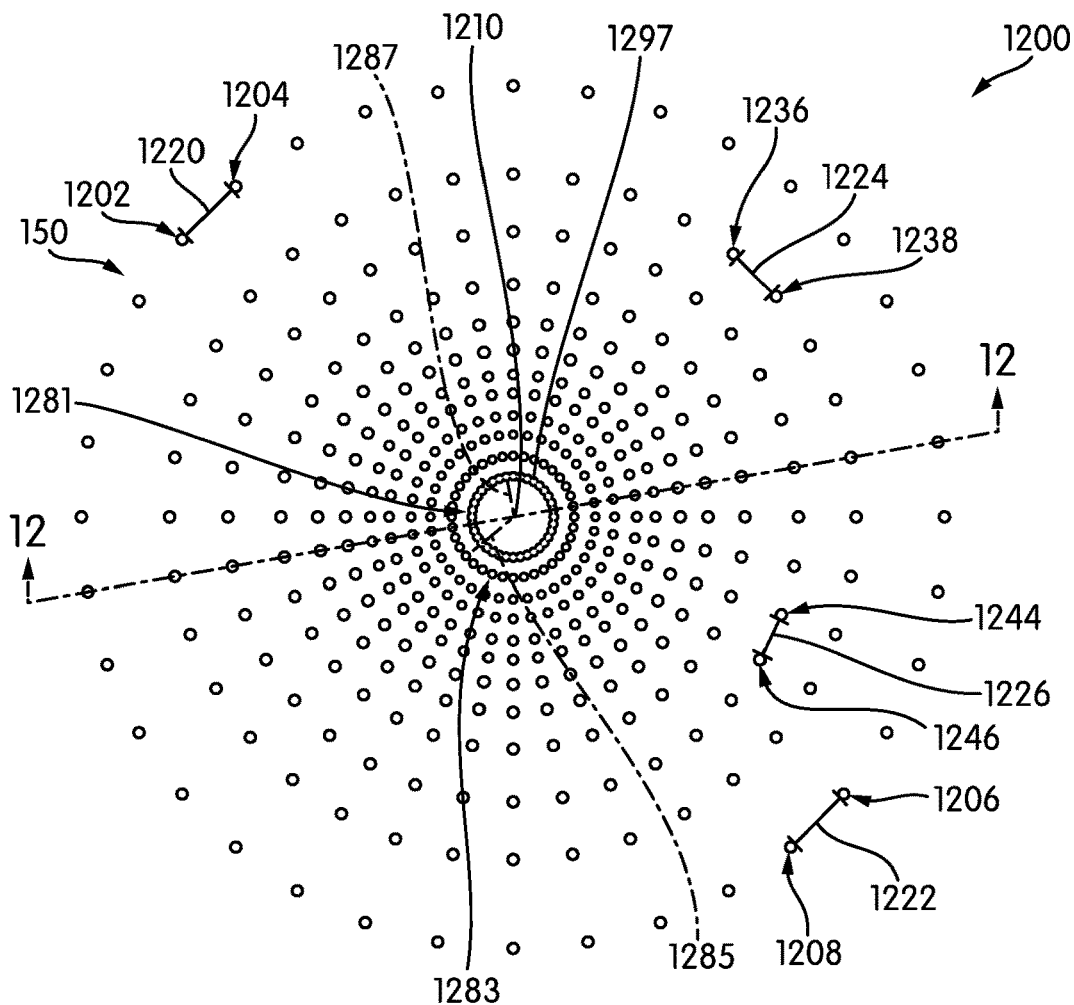
FIG. 12 is an isometric view of an embodiment of an aperture pattern.
Figure 12:
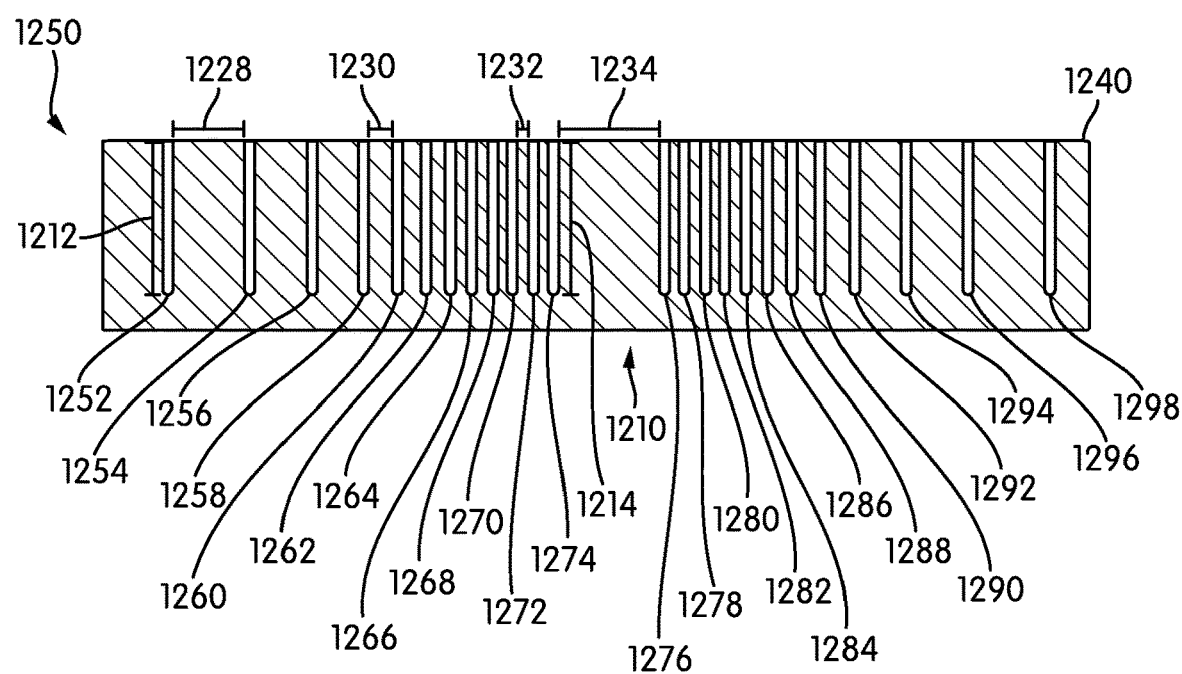

In FIG. 12, a regular third pattern ("third pattern") 1200 is shown. Similar to first pattern 1000 of FIG. 10 and second pattern 1100 of FIG. 11, third pattern 1200 has a generally round configuration, comprising a series of apertures 150 disposed in a repeated circular arrangement. As noted above, it should be understood that the pattern depicted in third pattern 1200 may include apertures 150 of various shapes and/or dimensions. Thus, apertures 150 may be round or another regular or irregular shape.

Furthermore, apertures 150 may comprise different lengths or have substantially similar lengths. For example, 24 apertures are depicted in a cross-sectional view 1250 of third pattern 1200 taken across the line 12-12. In cross-sectional view 1250, a first aperture 1252, a second aperture 1254, a third aperture 1256, a fourth aperture 1258, a fifth aperture 1260, a sixth aperture 1262, a seventh aperture 1264, an eighth aperture 1266, a ninth aperture 1268, a tenth aperture 1270, an eleventh aperture 1272, a twelfth aperture 1274, a thirteenth aperture 1276, a fourteenth aperture 1278, a fifteenth aperture 1280, a sixteenth aperture 1282, a seventeenth aperture 1284, an eighteenth aperture 1286, a nineteenth aperture 1288, a twentieth aperture 1290, a twenty-first aperture 1292, a twenty-second aperture 1294, a twenty-third aperture 1296, and a twenty-fourth aperture 1298 are shown. It should be understood that in other embodiments there may be a greater or lesser number of apertures disposed in third pattern 1200 than shown here.

In some embodiments, each aperture may have a length that differs from that of an adjacent aperture, or one or more apertures may have a substantially similar length. In some cases, apertures 150 may have a generally consistent length throughout third pattern 1200. For example, in cross-sectional view 1250 of FIG. 12, it can be seen that apertures 150 remain generally uniform in length as they approach a center 1210 (i.e., move in a radially inward direction), and also as they move radially outward (away from center 1210). For purposes of this disclosure, center 1210 may refer to the approximate origin of the circumference of apertures depicted. As an illustration, in some cases, first aperture 1252 can have a first length 1212 and twelfth aperture 1274 can have a second length 1214. In one embodiment, first length 1212 may be substantially similar to second length 1214. In other cases, all apertures in a pattern may have substantially similar lengths. In other words, apertures disposed along the same circumference and on different circumferences may be substantially similar in length to one another. However, in other embodiments, the lengths of apertures may differ from that shown here, may have a different repeated length pattern, or may have a random length arrangement.

In FIG. 12, it can be seen that the apertures can be spaced from neighboring apertures at varying distances. The distances between apertures may be varied based on whether the two apertures are disposed along a common circumference (i.e., are disposed at a similar radial distance from center 1210), or whether they are disposed along different circumferences.

As shown in FIG. 12, in some cases, there may be two or more apertures disposed adjacent to one another, but disposed on different circumferences. In cross-sectional view 1250, it can be seen that first aperture 1252 is spaced at a first radial distance 1228 from second aperture 1254, and fourth aperture 1258 is spaced at a second radial distance 1230 from fifth aperture 1260. In addition, tenth aperture 1270 is spaced at a third radial distance 1232 from eleventh aperture 1272, and twelfth aperture 1274 is spaced at a fourth radial distance 1234 from thirteenth aperture 1276. In some embodiments, first radial distance 1228 can be similar to or different from second radial distance 1230. In FIG. 12, first radial distance 1228 is substantially larger than either second radial distance 1230 or third radial distance 1232. Furthermore, second radial distance 1230 is greater than third radial distance 1232. In other words, apertures arranged along neighboring circumferences may be spaced apart at different distances.

In different embodiments, there may be a geometric pattern to the spacing between apertures. In some embodiments, the distances between apertures can decrease as they approach center 1210 (i.e., in a radially inward direction), and then increase again as they move radially outward (move away from center 1210). It should be understood that in other cases, the distances between apertures can increase as they approach center 1210 (i.e., in a radially inward direction), and then decrease again as they move radially outward. In one embodiment, the spacing between apertures can be mirrored. For example, the distance between two apertures can be substantially similar to the distance between two apertures disposed the opposite side (i.e., between apertures disposed along the same two neighboring circumferences). In other words, apertures disposed along the same two circumferences may be spaced at substantially similar distances from one another.

In some embodiments, there may be larger portions of a cushioning element that does not include apertures. For example, fourth radial distance 1234 can be greater than first radial distance 1228, second radial distance 1230, and/or third radial distance 1232. In one embodiment, fourth radial distance 1234 may represent the diameter of the circumference in which twelfth aperture 1274 and thirteenth aperture 1276 are arranged. In one embodiment, fourth radial distance 1234 may be approximately twice as large as third radial distance 1232. In other embodiments, fourth radial distance 1234 may be more than twice as great as third radial distance 1232. In other words, center 1210 may be associated with a portion of a cushioning element that does not include apertures. In one embodiment, the distance extending between twelfth aperture 1274 and thirteenth aperture 1276 may be larger due to the absence of any additional apertures. In other embodiments, fourth radial distance 1234 can be less than or similar to first radial distance 1228, second radial distance 1230, and/or third radial distance 1232.

Furthermore, in different embodiments, apertures disposed adjacent to one another and that share a common circumference can be spaced apart at regular or similar intervals. For example, in FIG. 12, a twenty-fifth aperture 1202 and a twenty-sixth aperture 1204 are separated by a first circumferential distance 1220, and a twenty-seventh aperture 1206 and a twenty-eighth aperture 1208 are separated by a second circumferential distance 1222. In some embodiments, first circumferential distance 1220 and second circumferential distance 1222 may be substantially similar, or they may differ. In FIG. 12, first circumferential distance 1220 and second circumferential distance 1222 are substantially similar. Thus, in some embodiments, apertures disposed along a common circumference may be spaced uniformly apart from one another.

Furthermore, the distance between neighboring apertures disposed along a first circumference can differ or be similar to the distance between neighboring apertures disposed along a second, different circumference. For example, a twenty-ninth aperture 1236 and a thirtieth aperture 1238 disposed on a common first circumference can be separated by a third circumferential distance 1224, and a thirty-first aperture 1244 and a thirty-second aperture 1246 disposed on a common second circumference are separated by a fourth circumferential distance 1226. In some embodiments, third circumferential distance 1224 and fourth circumferential distance 1226 can be similar. In other embodiments, third circumferential distance 1224 and fourth circumferential distance 1226 can differ. In FIG. 12, third circumferential distance 1224 is greater than fourth circumferential distance 1226.

As described with respect to FIG. 11, in some embodiments, a circumferential distance between two apertures may be close to zero or be approximately zero. In other words, two apertures can approach, touch, and/or merge with one another. For example, an innermost circumference 1297 includes a series of apertures whose edges are touching one another. In other words, each aperture of innermost circumference 1297 is disposed close enough to one another so as to form a substantially continuous opening similar to a siping. In some embodiments, apertures may be formed in various portions of a cushioning element to create a siping-like region, groove, or channel, through the cushioning element. While the arrangement can provide variations in cushioning, there may be other benefits, including enhanced traction or grip of the exterior surface. Various designs or flexible regions may also be formed by the inclusion of such siped apertures.

Thus, similar to first pattern 1000 in FIG. 10 and second pattern 1100 in FIG. 11, in some cases, a pattern can be formed whereby the distances between apertures disposed along a common circumference may decrease or increase along a direction. In one embodiment, in the direction extending from an outermost perimeter 1240 to center 1210, distance between apertures can decrease or increase. For example, in third pattern 1200, apertures that are disposed further radially outward are spaced apart at larger distances, while apertures that are disposed further radially inward are spaced apart at closer distances. Thus, in one embodiment, first circumferential distance 1220 may be greater than third circumferential distance 1224, and third circumferential distance 1224 may be greater than fourth circumferential distance 1226.

Figure 13:
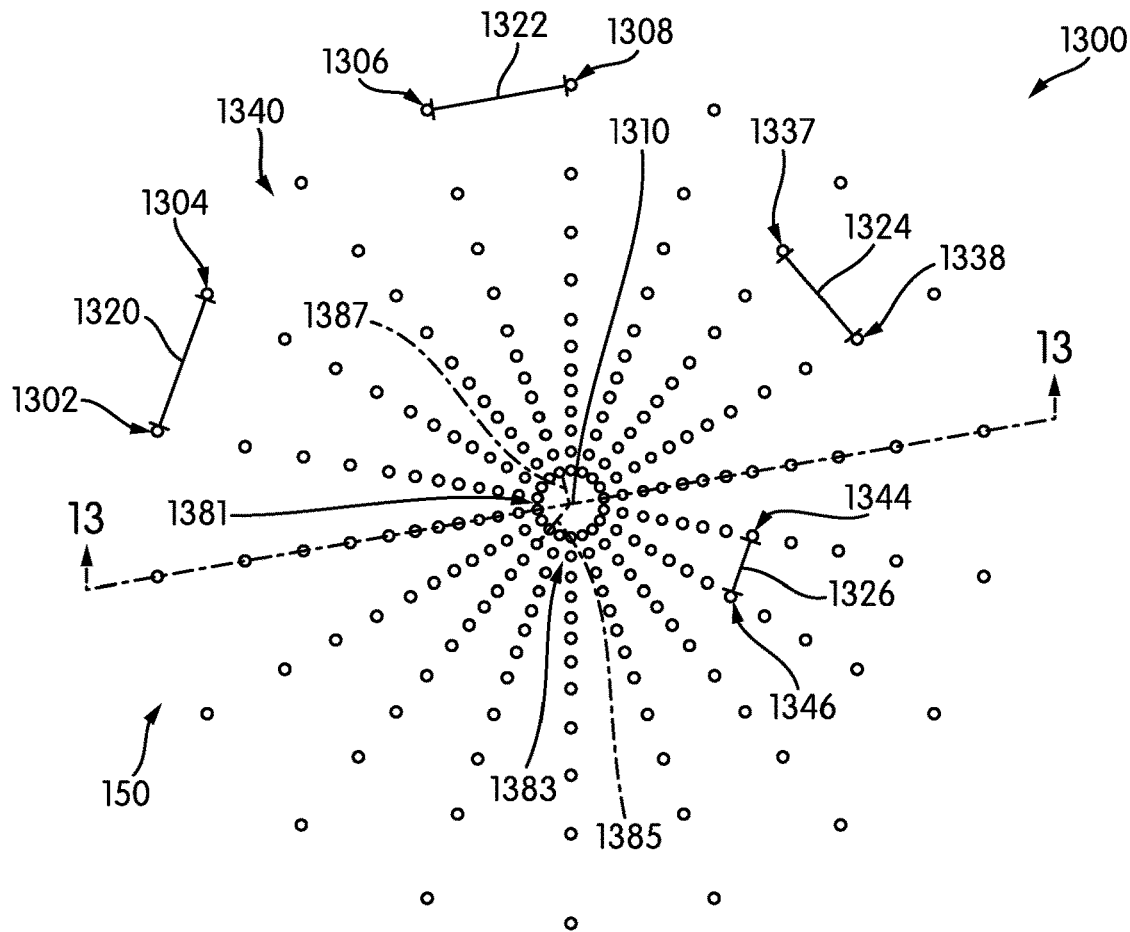
FIG. 13 is an isometric view of an embodiment of an aperture pattern.
Figure 13:
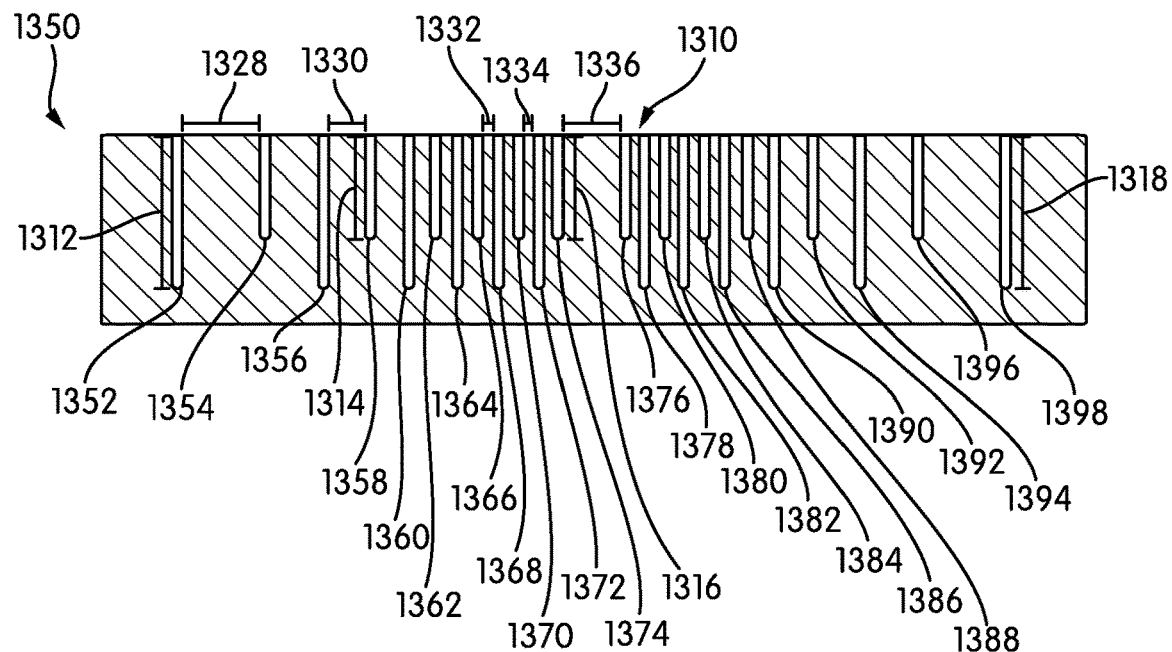

In FIG. 13, a regular fourth pattern ("fourth pattern") 1300 is shown. Similar to first pattern 1000 of FIG. 10, second pattern 1100 of FIG. 11, and third pattern 1200 of FIG. 12, fourth pattern 1300 has a generally round configuration, comprising a series of apertures 150 disposed in a repeated circular arrangement. As noted above, it should be understood that the pattern depicted in fourth pattern 1300 may include apertures 150 of various shapes and/or dimensions. Thus, apertures 150 may be round or another regular or irregular shape.

Furthermore, apertures 150 may comprise different lengths or have substantially similar lengths. For example, 24 apertures are depicted in a cross-sectional view 1350 of fourth pattern 1300 taken across the line 13-13. In cross-sectional view 1350, a first aperture 1352, a second aperture 1354, a third aperture 1356, a fourth aperture 1358, a fifth aperture 1360, a sixth aperture 1362, a seventh aperture 1364, an eighth aperture 1366, a ninth aperture 1368, a tenth aperture 1370, an eleventh aperture 1372, a twelfth aperture 1374, a thirteenth aperture 1376, a fourteenth aperture 1378, a fifteenth aperture 1380, a sixteenth aperture 1382, a seventeenth aperture 1384, an eighteenth aperture 1386, a nineteenth aperture 1388, a twentieth aperture 1390, a twenty-first aperture 1392, a twenty-second aperture 1394, a twenty-third aperture 1396, and a twenty-fourth aperture 1398 are shown. It should be understood that in other embodiments there may be a greater or lesser number of apertures disposed in fourth pattern 1300 than shown here.

In some embodiments, each aperture may have a length that differs from that of an adjacent aperture, or one or more apertures may have a substantially similar length. In some cases, apertures 150 may have a generally consistent length throughout fourth pattern 1300. For example, in cross-sectional view 1350 of FIG. 13, it can be seen that apertures 150 comprise an undulating pattern of lengths as they approach a center 1310 (i.e., in a radially inward direction), and also as they move radially outward. For purposes of this disclosure, center 1310 may refer to the approximate origin of the circumference of apertures depicted. As an illustration, in some cases, first aperture 1352 can have a first length 1312 and fourth aperture 1358 can have a second length 1314. In some cases, different apertures can have different lengths. In FIG. 13, first length 1312 is substantially greater than second length 1314. In addition, a third length 1316 is associated with twelfth aperture 1374. Third length 1316 may be substantially similar to second length 1314 in some embodiments. Furthermore, a fourth length 1318 may be substantially similar to first length 1312. In other words, there may be apertures with similar lengths throughout fourth pattern 1300. In FIG. 13, apertures are configured such that the lengths of alternating apertures (in a direction extending from an outermost perimeter 1340 toward center 1310) have similar lengths.

In other cases, all apertures in a pattern may have substantially similar lengths. In other words, apertures disposed along the same circumference and on different circumferences may be substantially similar in length to one another. However, in other embodiments, the lengths of apertures may differ from that shown here, may have a different repeated pattern, or may be random.

In FIG. 13, it can be seen that each aperture may be spaced at a distance from a neighboring aperture. In some embodiments, the distances between apertures 150 may vary. The distances between apertures may be varied based on whether the two apertures are disposed along a common circumference (i.e., are disposed at a similar radial distance from center 1310), or whether they are disposed along different circumferences.

As shown in FIG. 13, in some cases, there may be two or more apertures disposed adjacent to one another, but disposed on different circumferences. In cross-sectional view 1350, it can be seen that first aperture 1352 is spaced at a first radial distance 1328 from second aperture 1354, and third aperture 1356 is spaced at a second radial distance 1330 from fourth aperture 1358. In addition, eighth aperture 1366 is spaced from ninth aperture 1368 by a third radial distance 1332, and tenth aperture 1370 is spaced by a fourth radial distance 1334 from eleventh aperture 1372. Furthermore, twelfth aperture 1374 is spaced at a fifth radial distance 1336 from thirteenth aperture 1376. In some embodiments, the various radial distances can be similar to or different from one another. In FIG. 13, first radial distance 1328 is substantially larger than either second radial distance 1330, third radial distance 1332, or fourth radial distance 1334. Furthermore, second radial distance 1330 is greater than third radial distance 1332 and fourth radial distance 1334. In other words, apertures arranged along neighboring circumferences may be disposed at different distances from one another.

In different embodiments, there may be a geometric pattern to the spacing between apertures. In some embodiments, the distances between apertures can decrease as they approach center 1310 (i.e., in a radially inward direction), and then increase again as they move radially outward (move away from center 1310). It should be understood that in other embodiments, the distances between apertures can increase as they approach center 1310 (i.e., in a radially inward direction), and then decrease again as they move radially outward. In one embodiment, the spacing between apertures can be mirrored. For example, the distance between two apertures can be substantially similar to the distance between two apertures disposed the opposite side (i.e., between apertures disposed along the same two neighboring circumferences). In other words, apertures disposed along the same two circumferences may be spaced at substantially similar distances from one another.

In some embodiments, there may be larger portions of a cushioning element that does not include apertures. For example, fifth radial distance 1336 can be greater than first radial distance 1328, second radial distance 1330, third radial distance 1332, and/or fourth radial distance 1334. In one embodiment, fifth radial distance 1336 may represent the diameter of the circumference in which twelfth aperture 1374 and thirteenth aperture 1376 are arranged. In other embodiments, fifth radial distance 1336 can be less than first radial distance 1328, second radial distance 1330, third radial distance 1332, and/or fourth radial distance 1334. In one embodiment, fifth radial distance 1336 may be approximately twice as large as third radial distance 1332. In other embodiments, fifth radial distance 1336 may be more than twice as great as third radial distance 1332.

Thus, in some embodiments, there may be larger portions of a cushioning element that does not include apertures. For example, in one embodiment, the distance extending across from twelfth aperture 1374 to thirteenth aperture 1376 may be larger due to the absence of any additional apertures.

In different embodiments, apertures disposed adjacent to one another that share a common circumference can be spaced apart at regular or similar intervals. For example, in FIG. 13, a twenty-fifth aperture 1302 and a twenty-sixth aperture 1304 are separated by a first circumferential distance 1320, and a twenty-seventh aperture 1306 and a twenty-eighth aperture 1308 are separated by a second circumferential distance 1322. In some embodiments, first circumferential distance 1320 and second circumferential distance 1322 may be substantially similar or they may differ. In FIG. 13, first circumferential distance 1320 and second circumferential distance 1322 are substantially similar. Thus, in some embodiments, apertures disposed along a common circumference may be spaced uniformly apart from one another.

Furthermore, the distance between neighboring apertures disposed along a first circumference can differ or be similar to the distance between neighboring apertures disposed along a second circumference. For example, a twenty-ninth aperture 1337 and a thirtieth aperture 1338 disposed on a common first circumference can be separated by a third circumferential distance 1324, and a thirty-first aperture 1344 and a thirty-second aperture 1346 disposed on a common second circumference are separated by a fourth circumferential distance 1326. In some embodiments, third circumferential distance 1324 and fourth circumferential distance 1326 can be similar. In other embodiments, third circumferential distance 1324 and fourth circumferential distance 1326 can differ. In FIG. 13, third circumferential distance 1324 is greater than fourth circumferential distance 1326.

Thus, similar to the regular patterns described above in FIGS. 10-12, in some cases, a pattern can be formed whereby the distances between apertures disposed along a common circumference may decrease or increase along a direction. In one embodiment, in the direction extending from outermost perimeter 1340 to center 1310, the distance between apertures can decrease or increase. For example, in fourth pattern 1300, apertures that are disposed further radially outward are spaced apart at larger distances, while apertures that are disposed further radially inward are spaced apart at closer distances. In one embodiment, first circumferential distance 1320 may be greater than third circumferential distance 1324, and third circumferential distance 1324 may be greater than fourth circumferential distance 1326.

In different embodiments, it should be understood that each circumference described herein may include apertures disposed at a substantially similar radial distance from a center point. In other words, each circumferential pattern may have a plurality of apertures, and each of the plurality of apertures may be located at a substantially similar distance from the center of the circumferential pattern. Furthermore, referring to FIGS. 10-13. It can be seen that when two or more circumferential patterns are disposed adjacent to one another, in a manner where a first circumference evenly bounds a second circumference (i.e., each circumference shares a substantially similar center point), they may be distinguished by their respective differences in radial distance from the center.

For example, in FIG. 10, a first circumference 1081 comprising a first set of apertures is disposed in first pattern 1000. Generally bounding first circumference 1081 is a second circumference 1083 comprising a second set of apertures. Referring to cross-sectional view 1050, it may be understood that eighth aperture 1066 and ninth aperture 1068 are located along first circumference 1081. Furthermore, seventh aperture 1064 and tenth aperture 1070 are located along second circumference 1083. In some embodiments, each of the apertures comprising first circumference 1081 (including eighth aperture 1066 and ninth aperture 1068) may be disposed at a first radial distance 1087 from center 1010. In addition, in some embodiments, each of the apertures comprising second circumference 1083 (seventh aperture 1064 and tenth aperture 1070) may be disposed at a second radial distance 1085 from center 1010. Because center 1010 is being used as the reference point, in this case, first radial distance 1087 and second radial distance 1085 may be understood to refer to the approximate radius of each circumference. As shown in FIG. 10, in some embodiments, first radial distance 1087 may be less than second radial distance 1085. In other words, each of the apertures comprising first circumference 1081 may be disposed closer to center 1010 than each of the apertures comprising second circumference 1083. Furthermore, in one embodiment, each of the apertures comprising first circumference 1081 may be disposed at substantially the same radial distance from center 1010. In another embodiment, each of the apertures comprising second circumference 1083 may be disposed at substantially the same radial distance from center 1010.

Similarly, in FIG. 11, first circumference 1181 comprising a first set of apertures is disposed in second pattern 1100. Generally bounding first circumference 1181 is a second circumference 1183 comprising a second set of apertures. Referring to cross-sectional view 1150, it may be understood that eighth aperture 1166 and ninth aperture 1168 are located along first circumference 1181. Furthermore, seventh aperture 1164 and tenth aperture 1170 are located along second circumference 1183. In some embodiments, each of the apertures comprising first circumference 1181 (including eighth aperture 1166 and ninth aperture 1168) may be disposed at a first radial distance 1187 from center 1110. In addition, in some embodiments, each of the apertures comprising second circumference 1183 (seventh aperture 1164 and tenth aperture 1170) may be disposed at a second radial distance 1185 from center 1110. Because center 1110 is being used as the reference point, in this case, first radial distance 1187 and second radial distance 1185 may be understood to refer to the approximate radius of each circumference. As shown in FIG. 11, in some embodiments, first radial distance 1187 may be less than second radial distance 1185. In other words, each of the apertures comprising first circumference 1181 may be disposed closer to center 1110 than each of the apertures comprising second circumference 1183. Furthermore, in one embodiment, each of the apertures comprising first circumference 1181 may be disposed at substantially the same radial distance from center 1110. In another embodiment, each of the apertures comprising second circumference 1183 may be disposed at substantially the same radial distance from center 1110.

Referring to FIG. 12, a first circumference 1281 comprising a first set of apertures is disposed in third pattern 1200. Generally bounding first circumference 1281 is a second circumference 1283 comprising a second set of apertures. Referring to cross-sectional view 1250, it may be understood that twelfth aperture 1274 and thirteenth aperture 1276 are located along first circumference 1281. Furthermore, eleventh aperture 1272 and fourteenth aperture 1278 are located along second circumference 1283. In some embodiments, each of the apertures comprising first circumference 1281 (including twelfth aperture 1274 and thirteenth aperture 1276) may be disposed at a first radial distance 1287 from center 1210. Because center 1210 is being used as the reference point, in this case, first radial distance 1287 and second radial distance 1285 may be understood to refer to the approximate radius of each circumference. In addition, in some embodiments, each of the apertures comprising second circumference 1283 (including eleventh aperture 1272 and fourteenth aperture 1278) may be disposed at a second radial distance 1285 from center 1210. As shown in FIG. 12, in some embodiments, first radial distance 1287 may be less than second radial distance 1285. In other words, each of the apertures comprising first circumference 1281 may be disposed closer to center 1210 than each of the apertures comprising second circumference 1283. Furthermore, in one embodiment, each of the apertures comprising first circumference 1281 may be disposed at substantially the same radial distance from center 1210. In another embodiment, each of the apertures comprising second circumference 1283 may be disposed at substantially the same radial distance from center 1210.

Likewise, in FIG. 13, a first circumference 1381 comprising a first set of apertures is disposed in fourth pattern 1300. Generally bounding first circumference 1381 is a second circumference 1383 comprising a second set of apertures. Referring to cross-sectional view 1350, it may be understood that twelfth aperture 1374 and thirteenth aperture 1376 are located along first circumference 1381. Furthermore, eleventh aperture 1372 and fourteenth aperture 1378 are located along second circumference 1383. In some embodiments, each of the apertures comprising first circumference 1381 (including twelfth aperture 1374 and thirteenth aperture 1376) may be disposed at a first radial distance 1387 from center 1310. In addition, in some embodiments, each of the apertures comprising second circumference 1383 (including eleventh aperture 1372 and fourteenth aperture 1378) may be disposed at a second radial distance 1385 from center 1310. Because center 1310 is being used as the reference point, in this case, first radial distance 1387 and second radial distance 1385 may be understood to refer to the approximate radius of each circumference. As shown in FIG. 13, in some embodiments, first radial distance 1387 may be less than second radial distance 1385. In other words, each of the apertures comprising first circumference 1381 may be disposed closer to center 1310 than each of the apertures comprising second circumference 1383. Furthermore, in one embodiment, each of the apertures comprising first circumference 1381 may be disposed at substantially the same radial distance from center 1310. In another embodiment, each of the apertures comprising second circumference 1383 may be disposed at substantially the same radial distance from center 1310.

In different embodiments, each of the circumferential arrangements of apertures included in a pattern may be similarly disposed throughout the pattern. Thus, each circumference of apertures in first pattern 1000, second pattern 1100, third pattern 1200, and/or fourth pattern 1300 may include a series of apertures that are each disposed at a substantially similar radial distance from the center of the pattern.

As noted above, in different embodiments, a specific pattern may be selected and/or formed in the cushioning elements. In other embodiments, a plurality of apertures may be used and disposed in either a regular or irregular pattern along a portion of a cushioning element. In some embodiments, the apertures can be disposed over irregular intervals. For purposes of this disclosure, an irregular pattern refers to a generally inconsistent (or otherwise generally varying, nonrepeating, or random) arrangement of apertures. For example, a plurality of openings that are disposed in a generally random pattern or irregular shape may be irregularly arranged. It should be understood that some patterns may include both regular patterns and irregular patterns.

A few examples of irregular patterns that may be formed are depicted in FIGS. 14-19. It should be understood that these patterns are for illustrative purposes only, and any other pattern may be formed using the principles disclosed herein. In FIGS. 14-18, an irregular fifth pattern ("fifth pattern") 1400 is shown. It should be understood that in other embodiments there may be a greater or lesser number of apertures disposed in fifth pattern 1400 than shown here. Also, as noted above, it should be understood that the pattern depicted in fifth pattern 1400 may include apertures 150 of various shapes and/or dimensions. Thus, apertures 150 may be round or another regular or irregular shape. Furthermore, as described with reference to FIGS. 10-13, apertures 150 may comprise different lengths or have substantially similar lengths throughout fifth pattern 1400.

In different embodiments, the apertures in a pattern can be arranged to form various smaller configurations or subsets of apertures. In some embodiments, apertures 150 may be arranged in such a manner as to form one or more curved configurations. In one embodiment, apertures 150 can be disposed along a generally semi-circular shape, forming semi-circle arrangements. Referring to FIGS. 14-18, in some cases, one or more semi-circles of apertures, referred to hereafter as "semi-circles," may be disposed around a center 1410. In some embodiments, a pattern may be formed using one or more semi-circles.

In order to better represent the various arrangements of apertures 150 of fifth pattern 1400, a sequence of figures highlighting various portions of fifth pattern 1400 are depicted in FIGS. 14-18. For purposes of this disclosure, the term "highlighted" refers to the depiction of some apertures as darker relative to non-highlighted apertures in the illustrations. The difference in darkness or shading of the apertures shown in FIGS. 14-18 should thus not be taken to necessarily differentiate the apertures other than as identifying specific areas for purposes of reference during this discussion. To further facilitate the identification of specific aperture arrangements, there may be a curved line drawn over portions of the semi-circles, emphasizing the arrangement being defined.

Figure 14:
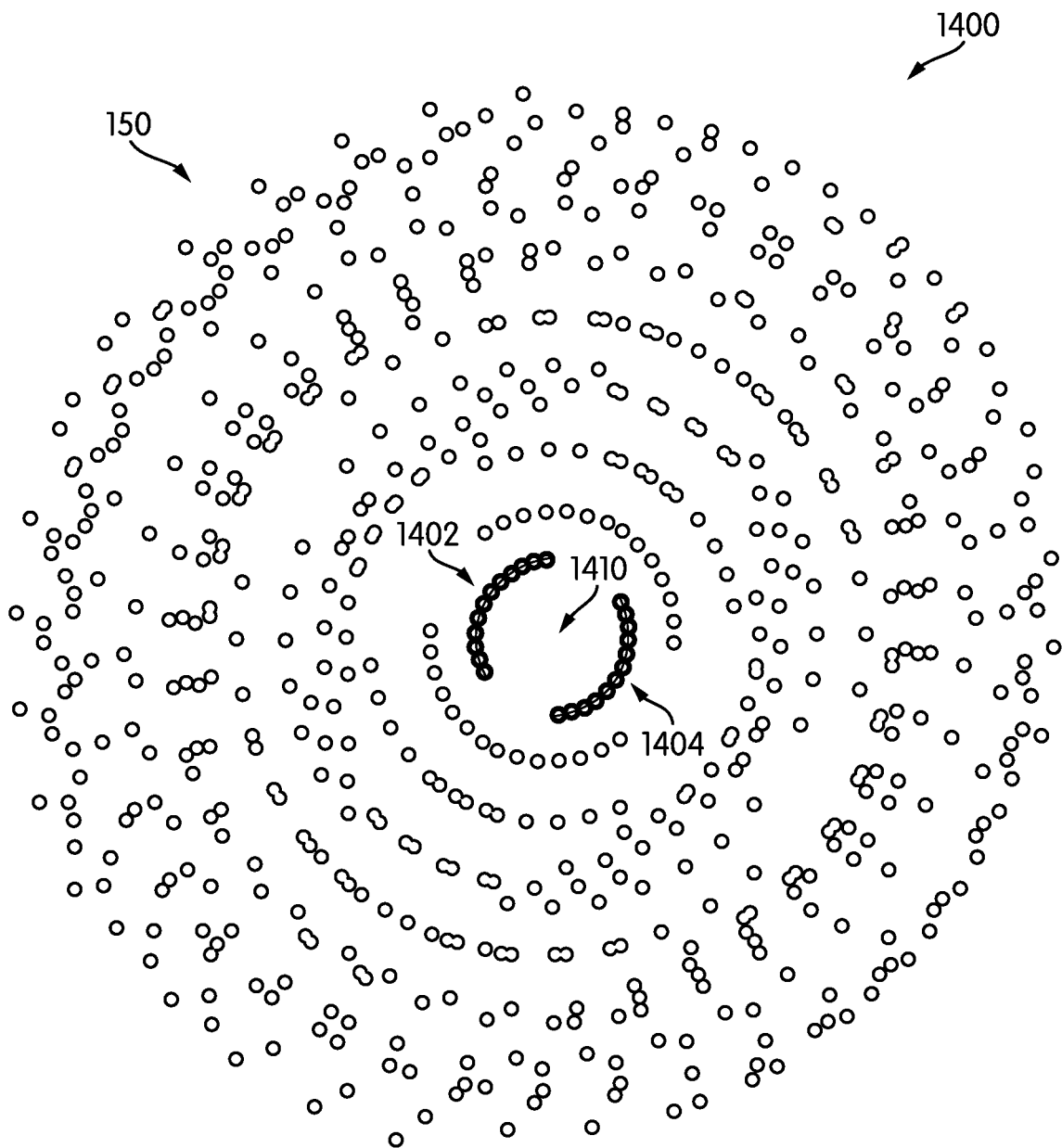
FIG. 14 is an isometric view of an embodiment of an aperture pattern.

In FIG. 14, a first semi-circle 1402 and a second semi-circle 1404 are shown highlighted. Similar to the discussion above regarding circumferences, apertures disposed along a common semi-circle may be aligned or disposed in a manner that forms a generally round or curved portion of a boundary. In some embodiments, apertures described as being located along the same semi-circle can be understood to mean that the apertures are disposed at a similar or nearly similar radial distance from center 1410. In some cases, this boundary can be solid, or the boundary can be dotted, or include gaps or openings.

Figure 15:
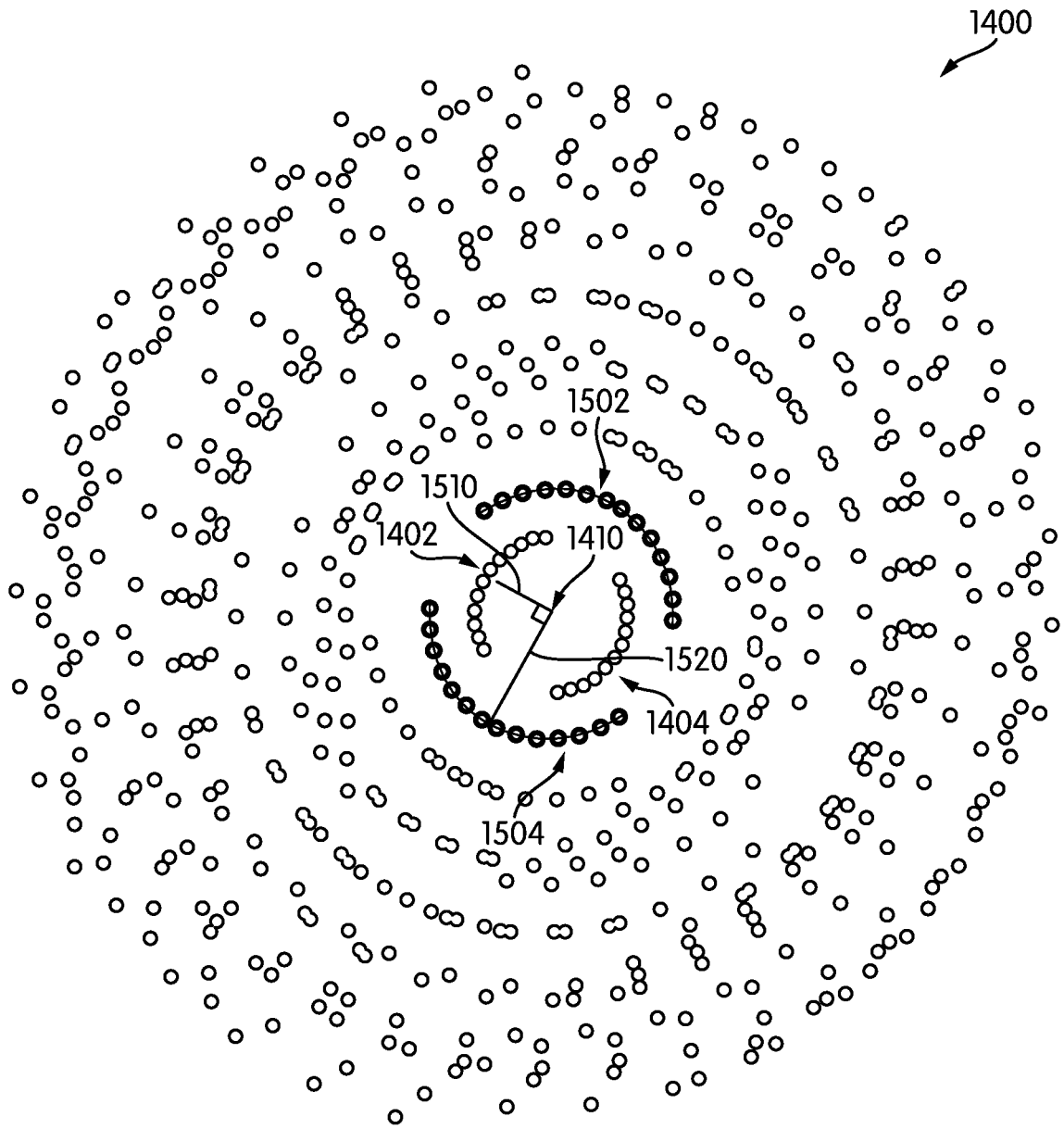
FIG. 15 is an isometric view of an embodiment of an aperture pattern.

In FIG. 15, two additional semi-circles are highlighted, comprising a third semi-circle 1502 and a fourth semi-circle 1504, disposed radially adjacent to first semi-circle 1402 and second semi-circle 1404. For purposes of this disclosure, "radially adjacent" refers to elements or arrangements of apertures that are disposed adjacent to one another but have generally different radial distances from center 1410. For example, the apertures of first semi-circle 1402 are disposed at an average first radial distance 1510 from center 1410, and the apertures of third semi-circle 1502 are disposed at an average second radial distance 1520 from center 1410. In some embodiments, first radial distance 1510 and second radial distance 1520 may differ. In FIGS. 14 and 15, first radial distance 1510 is smaller than second radial distance 1520. In other embodiments, first radial distance 1510 may be greater than or equal to second radial distance 1520.

Furthermore, in some embodiments, radially adjacent semi-circles can be arranged in a staggered or rotated configuration relative to one another. In the embodiment of FIG. 14-18, for example, first semi-circle 1402 and fourth semi-circle 1504 are staggered relative to each other. The degree of staggering or rotation may vary in different embodiments. For example, in some embodiments, semi-circles or other aperture arrangements can form an angle less than 90 and greater than 0 degrees with respect to one another. In other embodiments, semi-circles or other arrangements of apertures may form an angle of 90 degrees or greater with respect to one another. In FIG. 15, it can be seen that first semi-circle 1402 and fourth semi-circle 1504 are staggered approximately 90 degrees. However, in other embodiments, radially adjacent semi-circles may be disposed in a stacked configuration, such that the aperture arrangements are generally aligned with one another (see the repeating circumferences of FIGS. 10-13).

Figure 16:
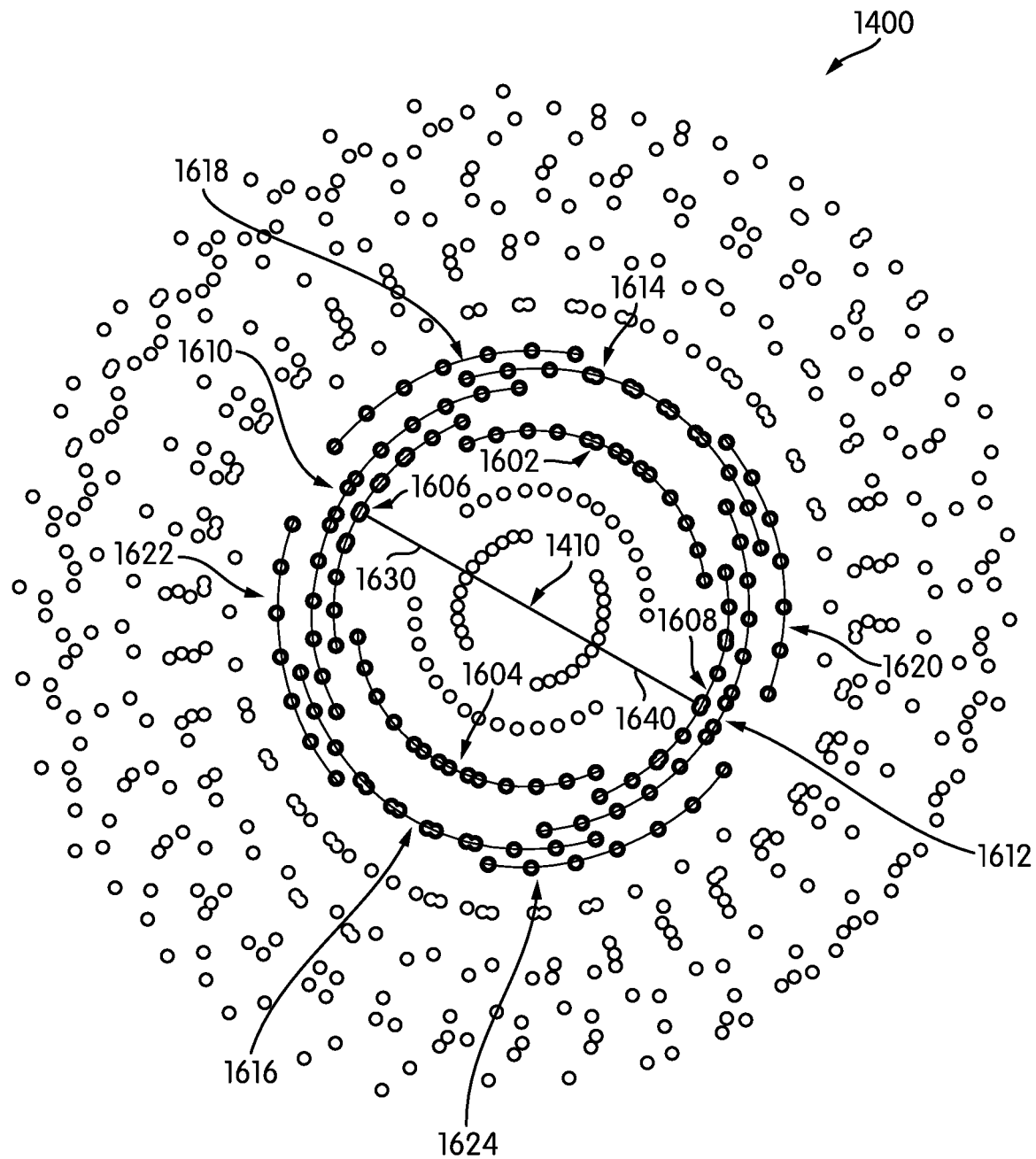
FIG. 16 is an isometric view of an embodiment of an aperture pattern.

In FIG. 16, 12 additional semi-circles are highlighted, comprising a fifth semi-circle 1602, a sixth semi-circle 1604, a seventh semi-circle 1606, an eighth semi-circle 1608, a ninth semi-circle 1610, a tenth semi-circle 1612, an eleventh semi-circle 1614, a twelfth semi-circle 1616, a thirteenth semi-circle 1618, a fourteenth semi-circle 1620, a fifteenth semi-circle 1622, and a sixteenth semi-circle 1624. In some embodiments, semi-circles can be disposed such that they form a pattern with one another relative to center 1410. In one example, the apertures of seventh semi-circle 1606 are disposed at an average third radial distance 1630 from center 1410, and the apertures of eighth semi-circle 1608 are disposed at an average fourth radial distance 1640 from center 1410. In some embodiments, third radial distance 1630 and fourth radial distance 1640 may be substantially similar. In other words, seventh semi-circle 1606 and eighth semi-circle 1608 can be arranged to create a pattern along a shared circumference. In one embodiment, seventh semi-circle 1606 and eighth semi-circle 1608 can be disposed in a mirrored orientation relative to center 1410. However, in other embodiments, seventh semi-circle 1606 and eighth semi-circle 1608 can be disposed in any position along the cushioning element. In another embodiment, three or more semi-circles can be oriented in repeated patterns around center 1410. For example, thirteenth semi-circle 1618, fourteenth semi-circle 1620, fifteenth semi-circle 1622, and sixteenth semi-circle 1624 may be arranged in a quartered-pattern, such that thirteenth semi-circle 1618 is disposed opposite from (mirroring) sixteenth semi-circle 1624, and fourteenth semi-circle 1620 is disposed opposite from (mirroring) fifteenth semi-circle 1622.

Figure 17:
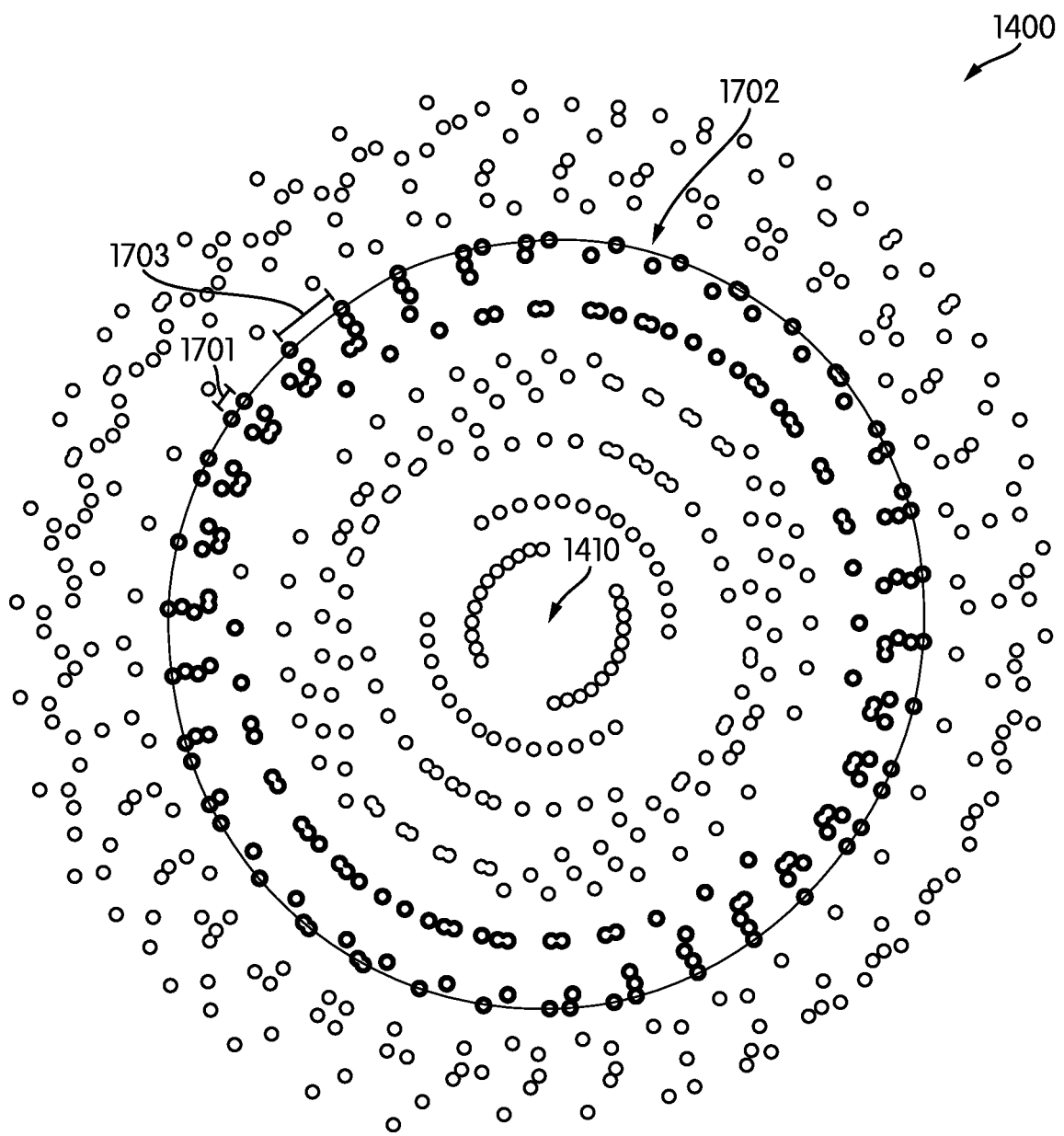
FIG. 17 is an isometric view of an embodiment of an aperture pattern.

In addition, in some embodiments, apertures in irregular patterns may form different shapes. For example, in FIG. 17, eight additional semi-circles are highlighted, as well as a first circle 1702. In some embodiments, there may be a generally discontinuous or continuous shape formed, as in FIGS. 10-13. In FIG. 17, first circle 1702 includes apertures that are arranged to create a discontinuous boundary around center 1410, similar to the arrangement of apertures in circumferences described with reference to FIGS. 10-13.

Figure 18:
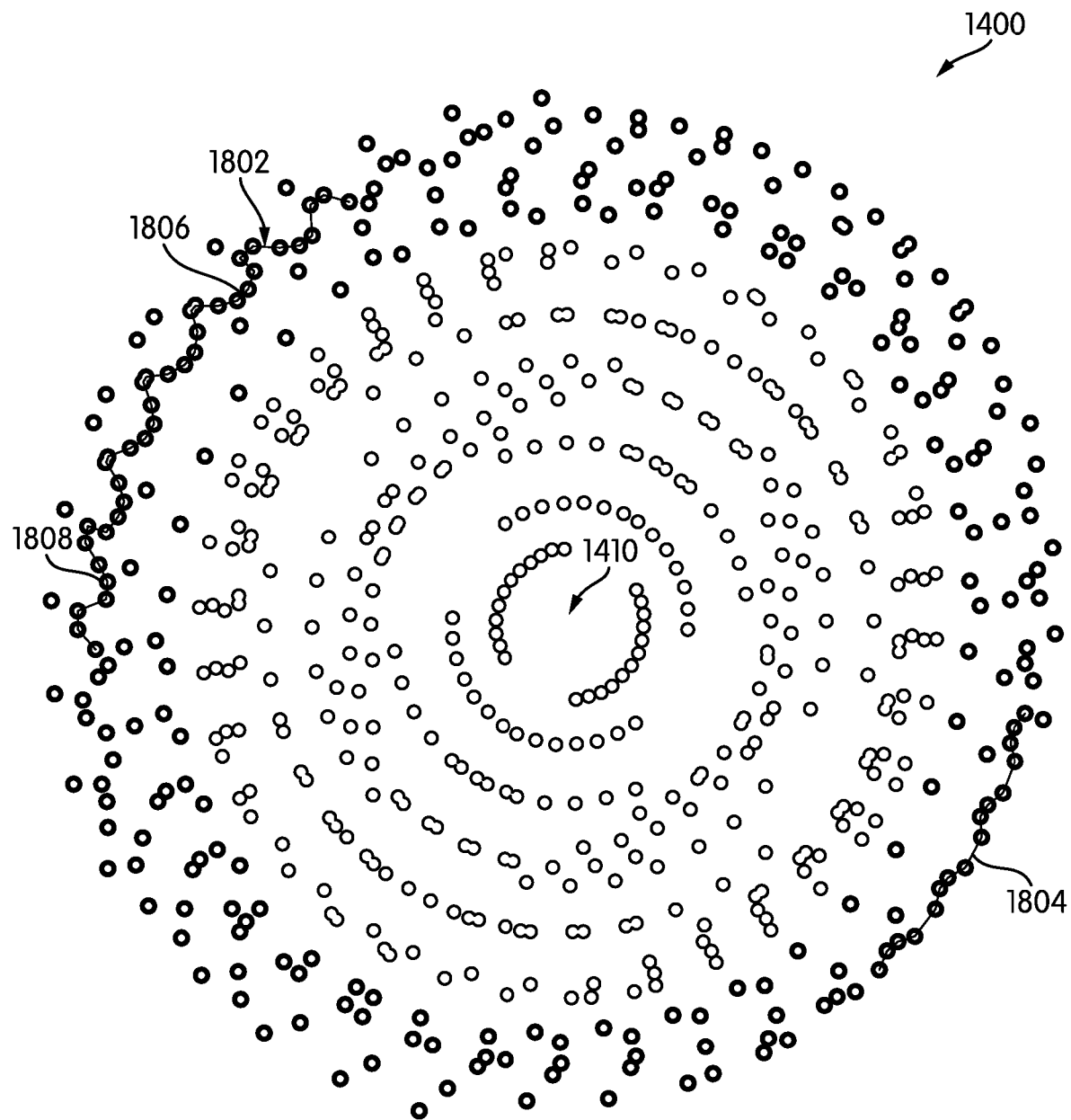
FIG. 18 is an isometric view of an embodiment of an aperture pattern.

In FIG. 18, additional apertures arranged in a variety of curved or non-linear configurations have been highlighted, including a first outer curve 1802 and a second outer curve 1804. It should be understood that apertures may form partial shapes or boundaries that are oriented differently from the semi-circles described thus far in different embodiments. For example, in FIG. 18, first outer curve 1802 includes multiple curved regions of apertures. Some of the curved regions may differ from others, as seen in a first curve 1806 and a second curve 1808, which each include differently arranged apertures.

Referring again to FIGS. 14-18, in different embodiments, apertures disposed adjacent to one another that share a common semi-circle can be spaced apart at varying intervals or distances. For example, in FIG. 14, apertures disposed along first semi-circle 1402 are closely arrayed such that they contact or touch one another. Thus, the circumferential distance can be approximately zero. In other words, each aperture of first semi-circle 1402 is disposed close enough to each other so as to form a substantially continuous opening similar to a siping. In another example, first circumferential distance 1020 between seventeenth aperture 1084 and eighteenth aperture 1086 in FIG. 10 can be approximately zero, such that a continuous aperture is formed.

In different embodiments, this siping facsimile can be a result of the varying degrees of merging between adjoining apertures. In some embodiments, apertures may be formed in various portions of a cushioning element to create a siping-like region, groove, or channel, through the cushioning element. While the arrangement can provide variations in cushioning, there may be other benefits, including enhanced traction or grip of the exterior surface. Various designs or flexible regions may also be formed by the inclusion of such siped apertures.

However, in other embodiments, the distance between neighboring apertures disposed along the same semi-circle can differ. In one embodiment, referring to first circle 1702 in FIG. 17, it can be seen that while some apertures contact one another (creating a merged region), other apertures in first circle 1702 are spaced apart from one another. For example, first circle 1702 includes a first pair and a second pair of apertures. The apertures of the first pair are spaced at a first distance 1701 from one another, and the apertures of the second pair are disposed at a second distance 1703 from one another. In some embodiments, first distance 1701 may differ from second distance 1703. In FIG. 17, first distance 1701 is smaller than second distance 1703. In other embodiments, first distance 1701 may be greater than or equal to second distance 1703.

Thus, different pairs of apertures disposed along a shared semi-circle may be arranged to have varying or irregular distances relative to one another. Similarly, the distances between apertures disposed along different semi-circles can vary. For example, referring to FIG. 15, the apertures of third semi-circle 1502 are disposed further apart than the apertures of first semi-circle 1402.

Figure 19:
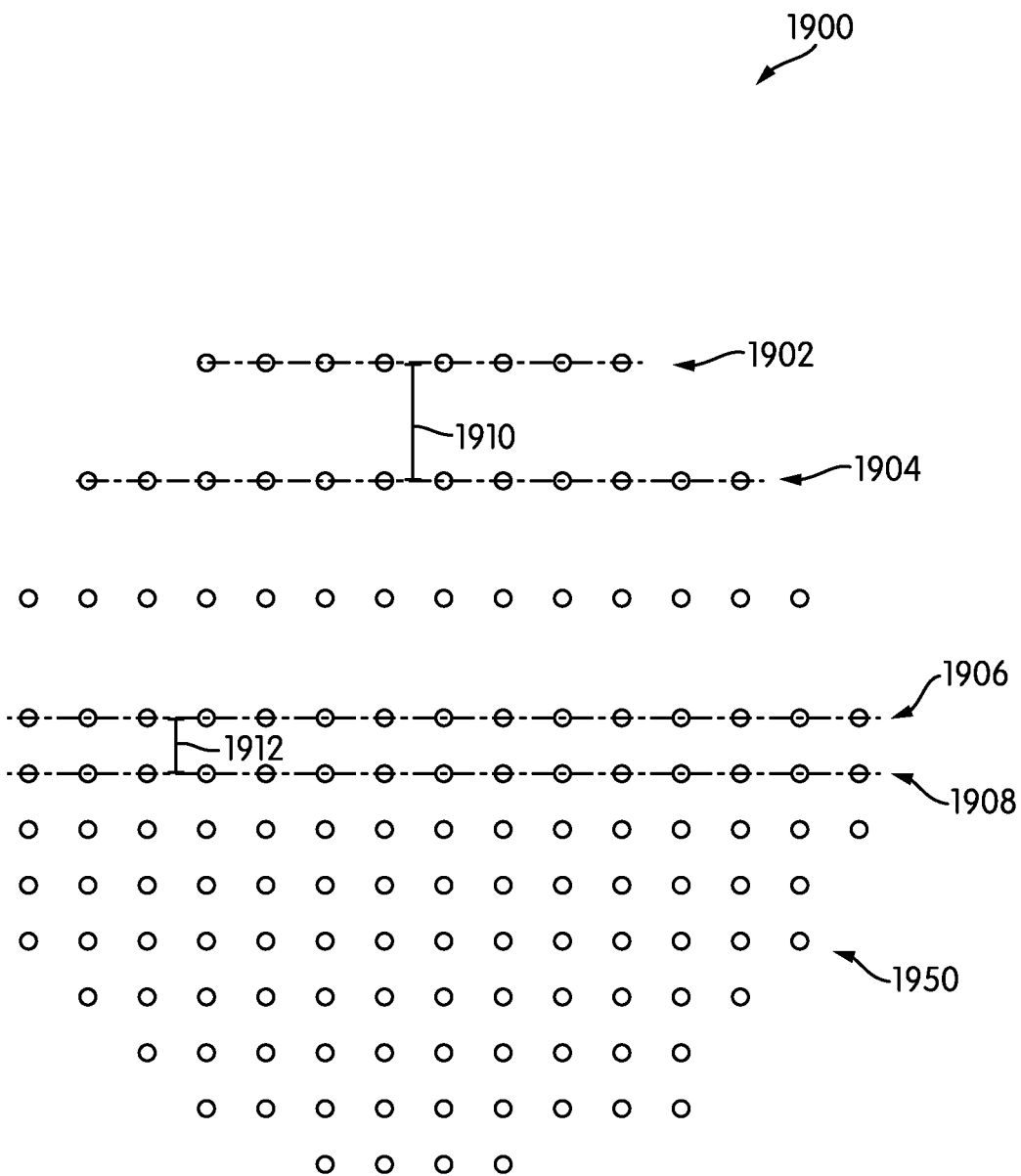
FIG. 19 is an isometric view of an embodiment of an aperture pattern.

Another embodiment of a possible irregular pattern of apertures is depicted in FIG. 19. In FIG. 19, a sixth pattern 1900 is illustrated, including a plurality of aperture rows 1950. Aperture rows 1950 may extend various distances across sixth pattern 1900, and may comprise any of the features, characteristics, and/or configurations described above with reference to FIGS. 10-18. In FIG. 19, sixth pattern 1900 includes a first row 1902, a second row 1904, a third row 1906, and a fourth row 1908. As shown in FIG. 19, in some cases, apertures may be arranged to have generally linear configurations or designs.

In different embodiments, aperture rows 1950 may be disposed in various configurations with respect to one another. In some embodiments, two or more aperture rows 1950 may be generally parallel to one another, as depicted in FIG. 19. In other embodiments, aperture rows 1950 may be disposed to form different angles with respect to one another.

Furthermore, adjacent aperture rows 1950 may be arranged at various distances from each other. For example, there may be an average first distance 1910 between first row 1902 and second row 1904, and an average second distance 1912 between third row 1906 and fourth row 1908. In some embodiments, first distance 1910 may be greater than second distance 1912, as depicted in FIG. 19. In other embodiments, first distance 1910 may be less than or equal to second distance 1912.

It should be understood that each semi-circle or aperture arrangement may include varying numbers of apertures. Referring to FIGS. 14 and 16, for example, first semi-circle 1402 includes 12 apertures, and ninth semi-circle 1610 includes 14 apertures. In another example, in the embodiment of FIG. 19, first row 1902 includes eight apertures, second row 1904 includes 12 apertures, the row between the second row 1904 and the third row 1906 includes 14 apertures, and third row 1906 includes 15 apertures. The number of apertures may be adjusted to create varying shapes in sixth pattern 1900. In FIG. 19, sixth pattern 1900 has the approximate (rough) shape or outline of a circle. In other embodiments, the number of apertures in any of these types of arrangements may differ to include more or fewer apertures than those depicted here, and/or to approximately form any other shape, such as square, oval, elliptical, diamond, rectangular, triangular, star, pentagonal, or any other regular or irregular shapes.

As noted above, the cushioning elements described herein may be utilized with various components or articles. For example, the degree of elasticity, cushioning, and flexibility of a sole component such as a sole member can be important factors associated with comfort and injury prevention for an article of footwear. FIGS. 20-23 depict an embodiment of a method of designing a customized sole member for an article of footwear.

Figure 20:
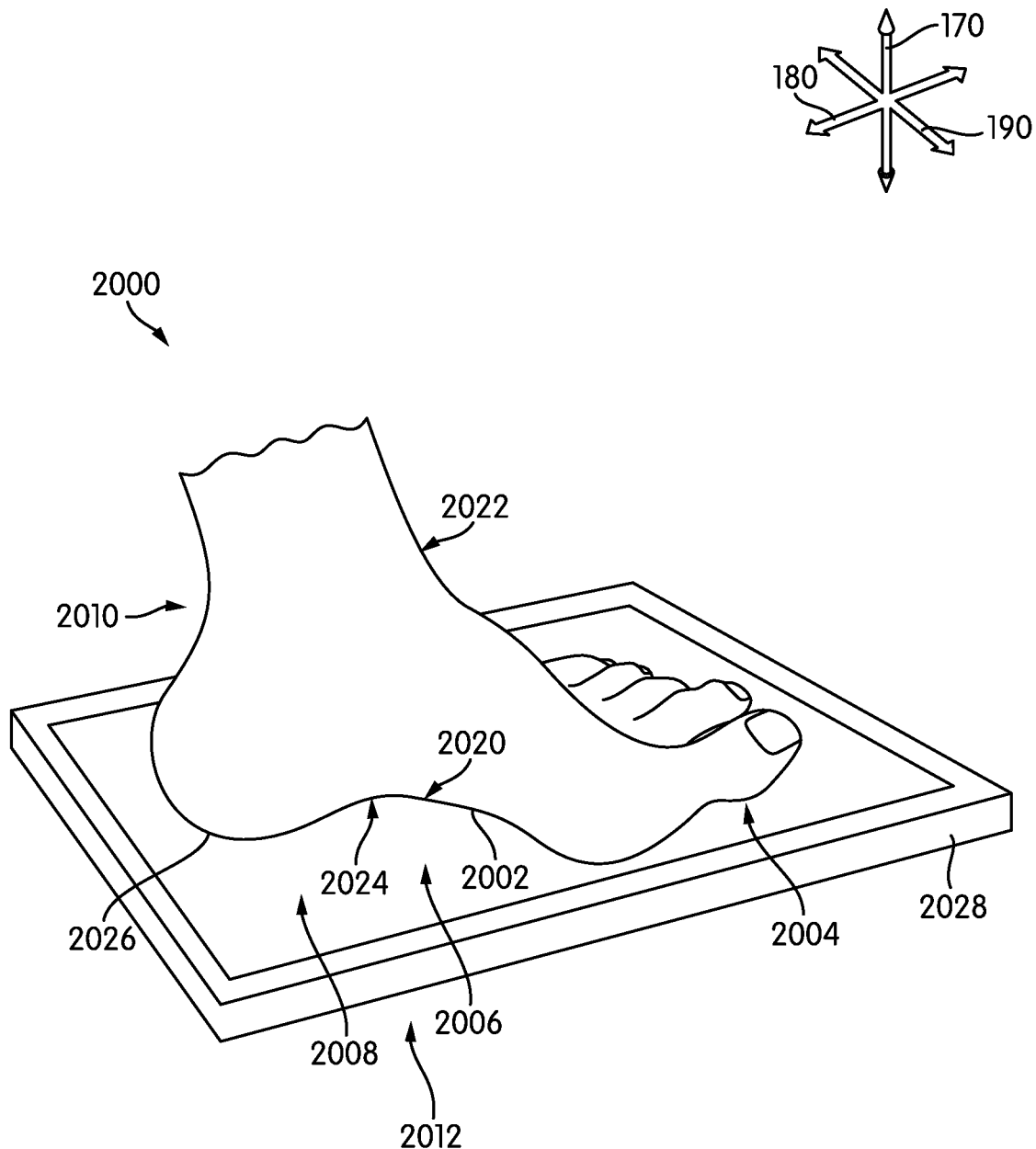
FIG. 20 illustrates an embodiment of the use of a device for obtaining three-dimensional foot data.

FIG. 20 shows the three-dimensional shape of plantar surface 2002 of a foot 2000 being measured using a data collection apparatus 2028. In some cases, data collection apparatus 2028 can be a force platform. In other cases, data collection apparatus 2028 can comprise one of the commercially available systems for measuring plantar pressure (e.g., Emed sensor platform, Pedar insole system, F-Scan system, Musgrave footprint system, etc.). Plantar pressure measurement systems can provide a means of obtaining specialized information regarding a foot that can be used to customize footwear for individuals. In some embodiments, the magnitude of pressure can be determined by dividing the measured force by the known area of the sensor or sensors evoked while the foot was in contact with the supporting surface in some embodiments.

For purposes of reference, foot 2000, representations of foot 2000, components associated with foot 2000 (such as an article of footwear, an upper, a sole member, a computer-aided design of foot 2000, and other components/representations) may be divided into different regions. Foot 2000 may include a forefoot region 2004, a midfoot region 2006 and a heel region 2008. Forefoot region 2004 may be generally associated with the toes and joints connecting the metatarsals with the phalanges. Midfoot region 2006 may be generally associated with the metatarsals of a foot. Heel region 2008 may be generally associated with the heel of a foot, including the calcaneus bone. In addition, foot 2000 may include a lateral side 2010 and a medial side 2012. In particular, lateral side 2010 and medial side 2012 may be associated with opposing sides of foot 2000. Furthermore, both lateral side 2010 and medial side 2012 may extend through forefoot region 2004, midfoot region 2006, and heel region 2008. It will be understood that forefoot region 2004, midfoot region 2006, and heel region 2008 are only intended for purposes of description and are not intended to demarcate precise regions of foot 2000. Likewise, lateral side 2010 and medial side 2012 are intended to represent generally two sides of foot 2000, rather than precisely demarcating foot 2000 into two halves.

Figure 21:
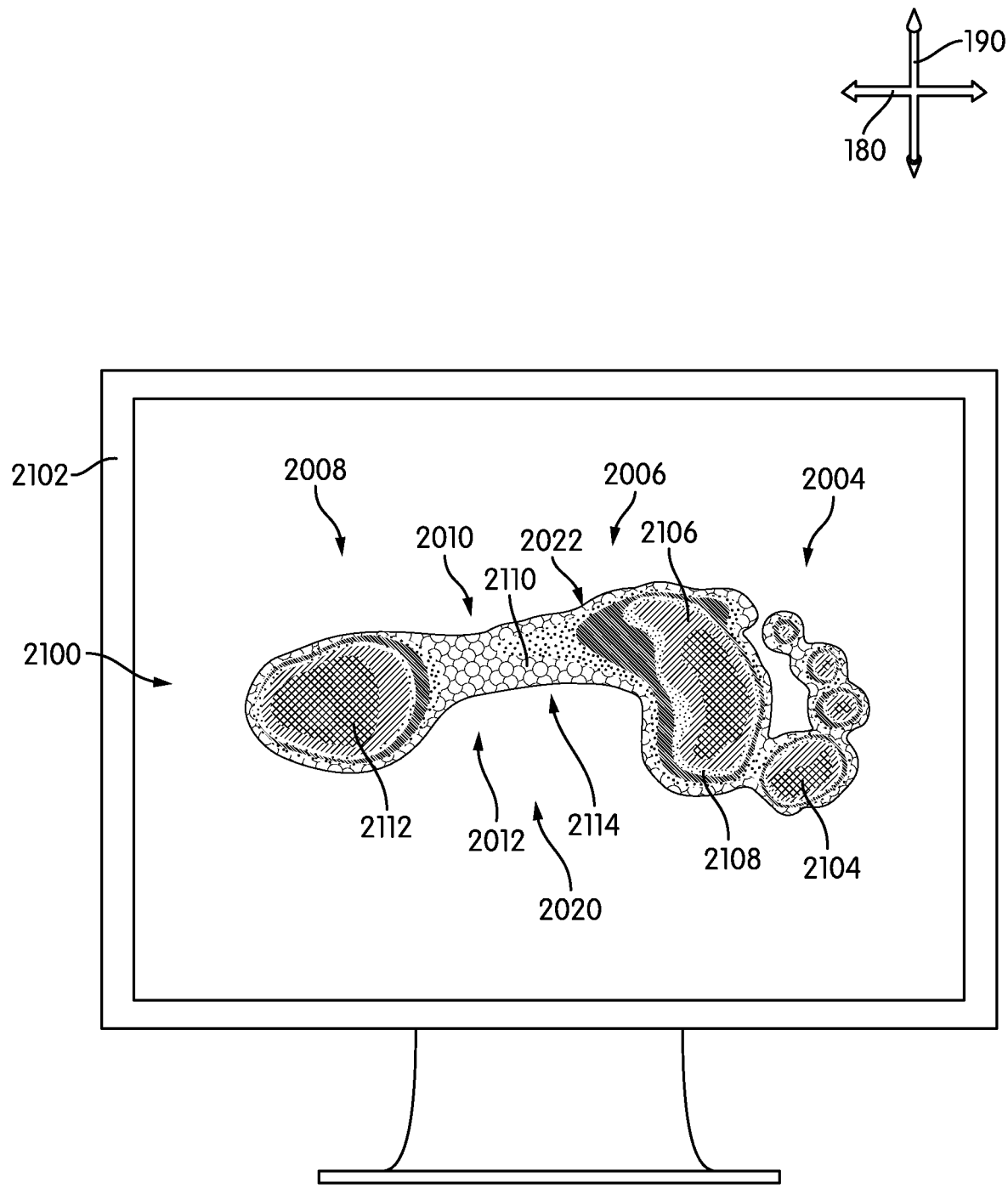
FIG. 21 schematically illustrates an embodiment of a virtual image of digitized three-dimensional foot data.

Furthermore, in the examples depicted in FIGS. 20 and 21, foot 2000 and/or a virtual scan 2100 of a foot may include a medial arch area 2020, associated with an upward curve along medial side 2012 of midfoot region 2006, and a lateral arch area 2022, associated with an upward curve along lateral side 2010 of midfoot region 2006. The region corresponding to lateral arch area 2022 is best seen in FIG. 21, which illustrates a computer screen or virtual image of digitized three-dimensional foot data. As described below, the curvature of medial arch area 2020 and lateral arch area 2022 may vary from one foot to another. In addition, foot 2000 includes a transverse arch 2024 that extends in a direction generally aligned with lateral axis 190 near forefoot region 2004 along plantar surface 2002. Foot 2000 also includes a heel prominence 2026, which is the prominence located in heel region 2008 of foot 2000. As shown in FIG. 20, foot 2000 is illustrated as a left foot; however, it should be understood that the following description may equally apply to a mirror image of a foot or, in other words, a right foot.

Although the embodiments throughout this detailed description depict components configured for use in athletic articles of footwear, in other embodiments, the components may be configured to be used for various other kinds of footwear including, but not limited to, hiking boots, soccer shoes, football shoes, sneakers, running shoes, cross-training shoes, rugby shoes, basketball shoes, baseball shoes as well as other kinds of shoes. Moreover, in some embodiments, components may be configured for various kinds of non-sports related footwear, including, but not limited to, slippers, sandals, high-heeled footwear, loafers as well as any other kinds of footwear.

Components associated with an article of footwear are generally made to fit various sizes of feet. In the embodiments shown, the various articles are configured with approximately the same footwear size. In different embodiments, the components could be configured with any footwear sizes, including any conventional sizes for footwear known in the art. In some embodiments, an article of footwear may be designed to fit the feet of a child. In other embodiments, an article of footwear may be designed to fit the feet of an adult. Still, in other embodiments, an article of footwear may be designed to fit the feet of a man or a woman.

Referring to FIGS. 20 and 21, a first step of the present method is to collect data related to foot 2000, such as using a barefoot pressure measurement or other data, from the foot being measured on data collection apparatus 2028. Data collection apparatus 2028 may include provisions for capturing information about an individual's feet. Specifically, in some embodiments, data collection apparatus 2028 may include provisions to capture geometric information about one or more feet. This geometric information can include size (e.g., length, width, and/or height) as well as three-dimensional information corresponding to the customer's feet (e.g., forefoot geometry, midfoot geometry, heel geometry, and ankle geometry). In at least one embodiment, the captured geometric information for a customer's foot can be used to generate a three-dimensional model of the foot for use in later stages of manufacturing. In particular, the customized foot information can include at least the width and length of the foot. In some cases, the customized foot information may include information about the three-dimensional foot geometry. Customized foot information can be used to create a three-dimensional model of the foot. Embodiments may include any other provisions for capturing customized foot information. The present embodiments could make use of any of the methods and systems for forming an upper disclosed in U.S. patent application Ser. No. 14/565,582, filed Dec. 10, 2014, titled "Portable Manufacturing System for Articles of Footwear," the entirety of which is hereby incorporated by reference.

Some embodiments could use any of the systems, devices, and methods for imaging a foot as disclosed in Leedy et al., U.S. Patent Publication Number 2013/0258085, published Oct. 3, 2013, and titled "Foot Imaging and Measurement Apparatus," (previously U.S. patent application Ser. No. 13/433,463, filed Mar. 29, 2012), the entirety of which is hereby incorporated by reference.

In FIG. 21, a screen 2102 displays virtual scan 2100 of plantar pressure distributions for the foot of FIG. 20. Virtual scan 2100 may provide a measured foot image or representation, including various distinct regions to indicate the pressures applied or experienced by foot 2000 over its plantar surface 2002, as shown in FIG. 20. In one example, pressures can include a first pressure area 2104, a second pressure area 2106, a third pressure area 2108, a fourth pressure area 2110, and a fifth pressure area 2112. An additional pressure area 2114 is indicated where plantar surface 2002 did not make an impressionable contact with the surface of data collection apparatus 2028. In some embodiments, colors (not shown in FIG. 21) can be included in virtual scan 2100 to more readily distinguish variations within the measured pressure data. It should be noted that in other embodiments, different, fewer, or more pressure areas may be measured or indicated.

As seen in FIG. 21, in some embodiments, the data collected may include virtual scan 2100 of foot 2000. In some embodiments, virtual scan 2100 may be used to assess the three-dimensional shape and obtain digital data in a two-dimensional or a three-dimensional reference frame. In other embodiments, virtual scan 2100 can provide a baseline shape for a footwear component. In one embodiment, three-dimensional scanned images may be used to measure the overall shape of a person's feet, and obtain two-dimensional measurements such as an outline, length, and width of foot 2000. Obtaining foot geometry can establish a baseline record for the person in one embodiment. In some embodiments, other input may also be provided to supplement information regarding the person being measured. In different embodiments, additional data such as toe height information may also be obtained. In other embodiments, plaster casts of a person's foot may be taken and digitized. Additionally, other digital or imaging techniques that may be employed to capture two- and three-dimensional foot shape and profile can be used to construct and/or supplement virtual scan 2100. In other embodiments, the person whose foot is being measured may provide answers to questions describing the person's physical characteristics, limitations, preferences, and/or personal lifestyle, which may impact design of the various parts described herein.

Figure 22:
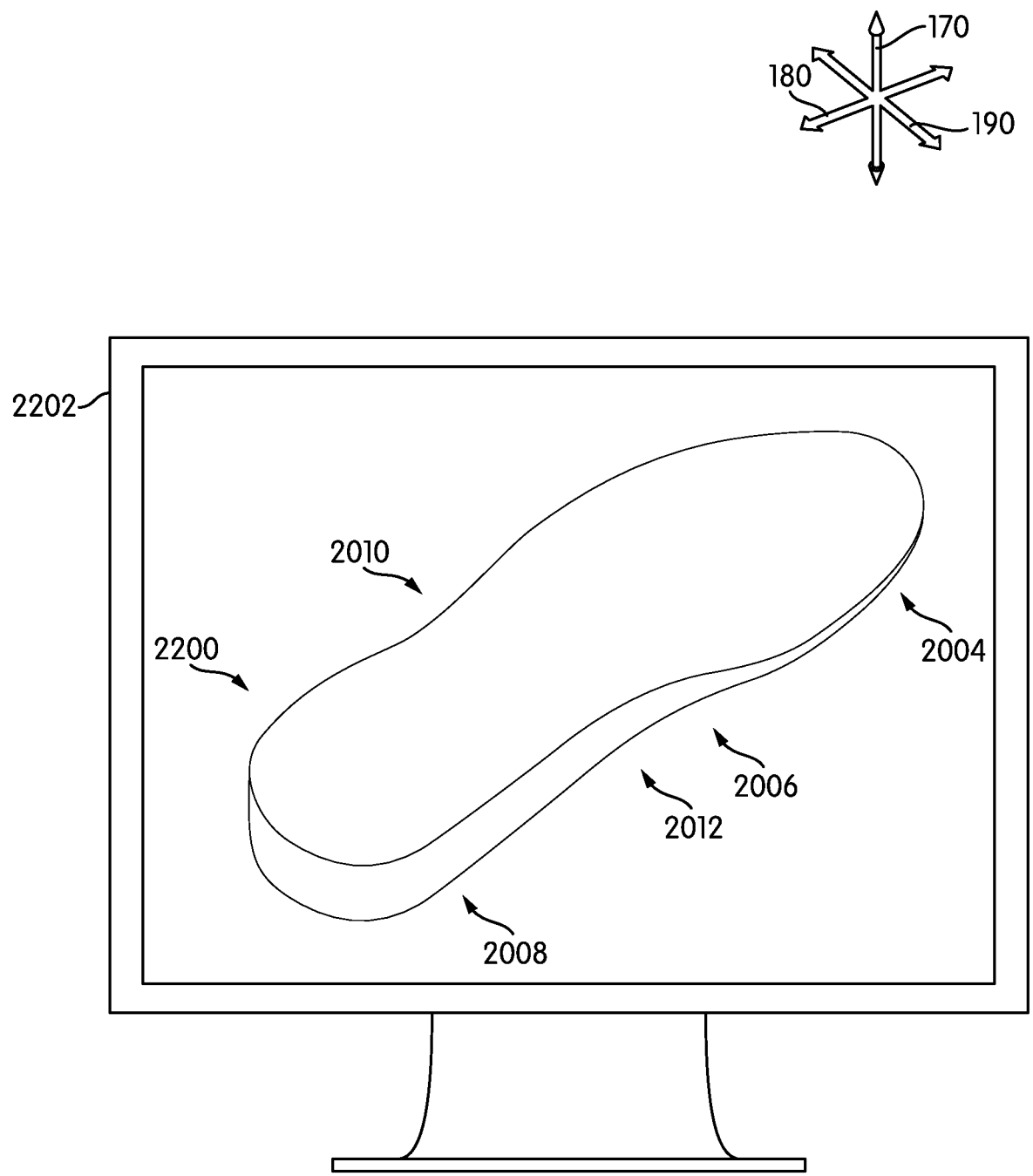
FIG. 22 schematically illustrates an embodiment of a virtual image of a template for a sole structure.
Figure 23:
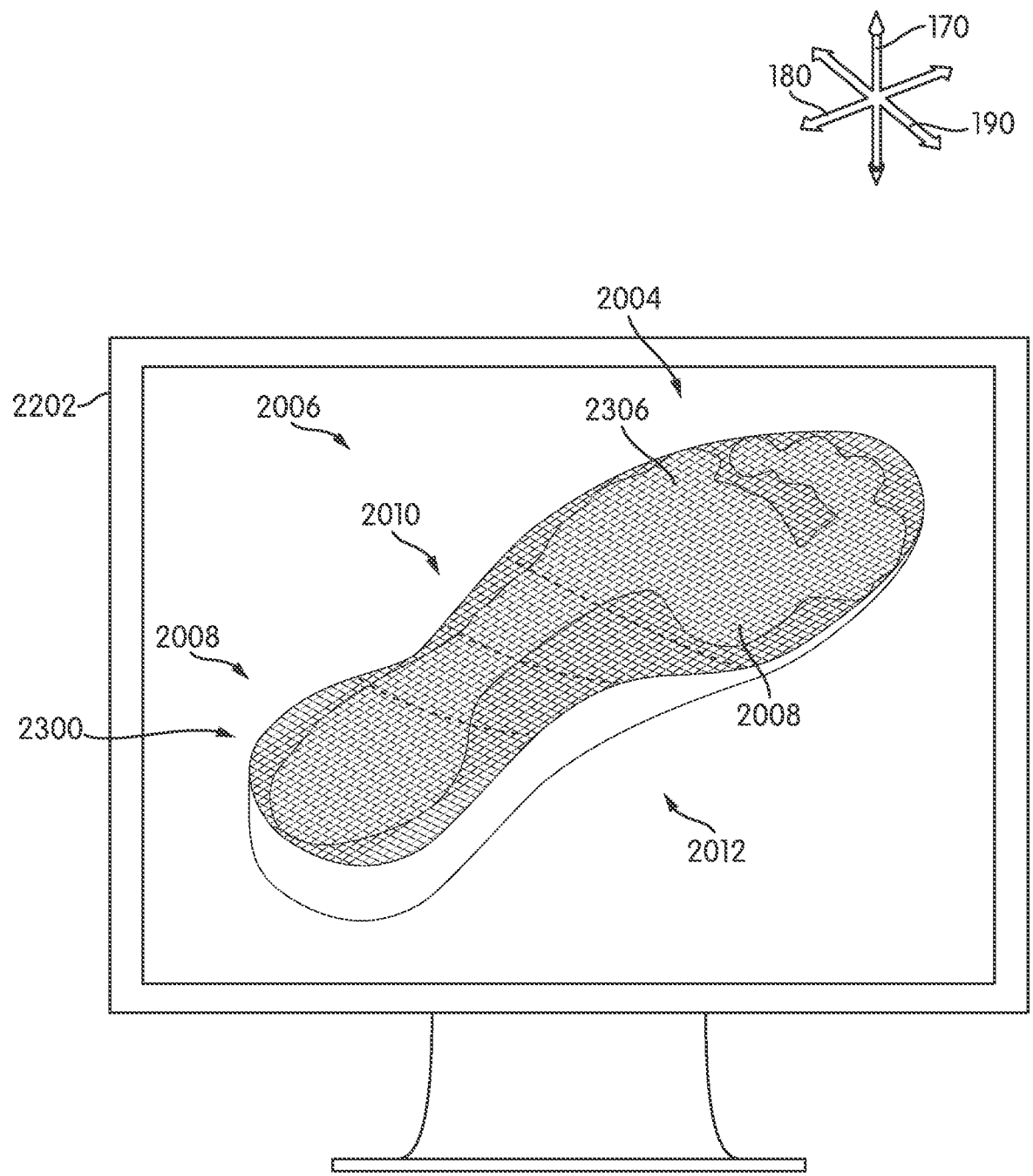
FIG. 23 schematically illustrates an embodiment of a virtual image of a customized sole structure.

In different embodiments, a sole member may provide one or more functions for an article of footwear. In FIG. 22, an image of a template of a sole member 2200 is displayed on a screen 2202. In some embodiments, sole member 2200 may attenuate ground reaction forces when compressed between the foot and the ground during walking, running, or other ambulatory activities. The configuration of sole member 2200 may vary significantly in different embodiments to include a variety of conventional or non-conventional structures. In some cases, the configuration of sole member 2200 can be selected or customized according to one or more types of ground surfaces on which sole member 2200 may be used. Examples of ground surfaces include, but are not limited to, natural turf, synthetic turf, dirt, as well as other surfaces.

Upon obtaining measurements of foot 2000 (see FIG. 20), sole member 2200 may be adjusted or altered in different embodiments. As seen in the virtual representation depicted in FIG. 23, using the data collected from the steps above, a first custom sole 2300 may be designed. In some embodiments, the design may utilize an application of an integrated computer-aided design such as a computer-automated manufacturing (CAD-CAM) process. Sole member 2200, or any other template previously selected, may be provided as an input to the computer design program. In one embodiment, the three-dimensional foot shape data from virtual scan 2100 in FIG. 21 is also provided to the program.

In different embodiments, virtual scan 2100 may provide information regarding foot shape and pressure to allow the appropriate fit and comfort within the article of footwear. The information may be used to form first custom sole 2300. In some embodiments, data from virtual scan 2100 may be superimposed or otherwise incorporated into the template of sole member 2200 (see FIGS. 21 and 22). For example, there may be a process of aligning the data representing the plantar pressures of foot 2000 with sole member 2200 and generating a partial or complete design of first custom sole 2300. In one embodiment, pressure contour lines 2306 may be generated during the design of first custom sole 2300. The pressure distribution may be adjusted to a "best-fit" position based upon user input in some embodiments. Once the distribution is finalized, a resiliency profile may be created. For purposes of this disclosure, a resiliency profile is a personalized pressure distribution for a user that may include the data collected during the steps described above. In some embodiments, the resiliency profile may be utilized in the production of first custom sole 2300. Thus, in one embodiment, after the resiliency profile comprising an individual's plantar pressure distributions is aligned with the template of sole member 2200, a customized sole member may be formed or manufactured.

It should be understood that, in different embodiments, the design of a sole member may include various modifications. Customized modifications may provide individual users with a wider range of comfort and fit. For example, different users may have differences in the height of the arch of foot 2000. As described above, foot 2000 may include multiple arches. Generally, the arch is a raised curve on the bottom surface of foot 2000. When the tendons of foot 2000 pull a normal amount, foot 2000 generally forms a moderate or normal arch. However, when tendons do not pull together properly, there may be little or no arch. This is called "flat foot" or fallen arch. Over-pronation of a foot may be common for those with flat feet. The framework of a foot can collapse, causing the foot to flatten and adding stress to other parts of the foot. Individuals with flat feet may need orthotics to control the flattening of the foot. Moreover, the opposite may also occur, though high foot arches are less common than flat feet. Without adequate support, highly arched feet tend to be painful because more stress is placed on the section of the foot between the ankle and toes. This condition can make it difficult to fit into shoes. Individuals who have high arches usually need foot support. It should be noted that such variations in arch height are one of many possible examples of customized foot geometry that may be incorporated into a design.

Figure 24:
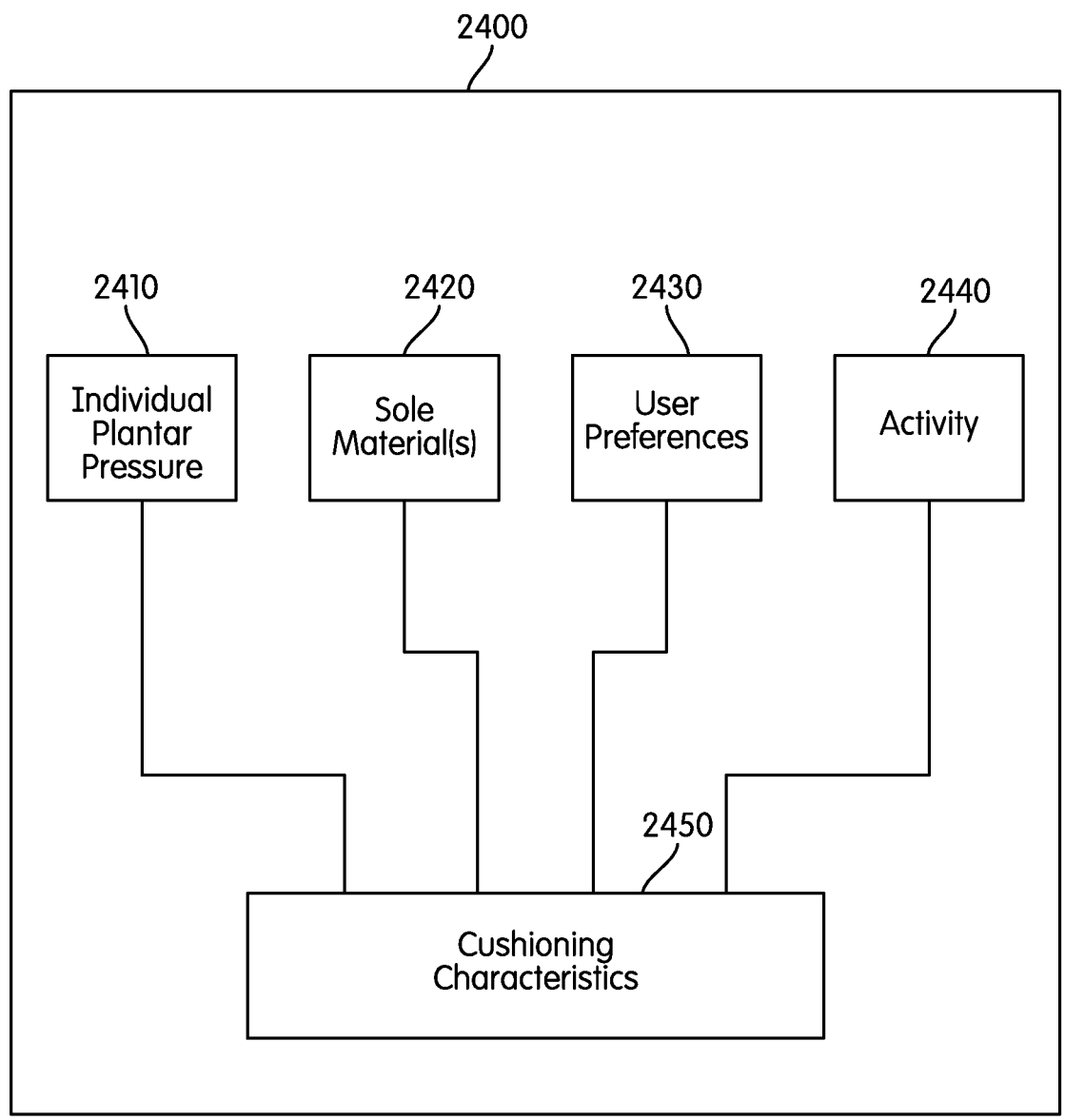
FIG. 24 is an isometric view of an embodiment of a sole member during a process of forming apertures.

Referring to FIG. 24, an embodiment of an influence diagram 2400 is depicted. Influence diagram 2400 reflects some of the factors or variables that can be considered, incorporated, and/or used during the generation of the resiliency profile, permitting customization of cushioning characteristics 2450 of a sole member. For example, a first factor 2410 includes an individual's measured plantar pressure for each foot, which was discussed above with respect to FIGS. 20-21. In addition, a second factor 2420 may include the materials that will be used to form the custom sole member. Third factor 2430 can be the individual user's own personal preferences regarding the type or level of cushioning desired. Fourth factor 2440 may be the activity or sport that the user will be generally engaging in while using the custom sole member. In some cases, the sole member can be designed or tailored to provide special cushioning in areas or regions of the sole member that typically experience more force or pressure from the foot during specific activities. Thus, in some embodiments, one or more of these factors can contribute to cushioning characteristics 2450 of a sole member. It should be understood that influence diagram 2400 is provided as an example, and many other factors not listed here may be included in other embodiments. Furthermore, one or more factors listed in influence diagram 2400 may be removed from consideration depending on the desired output or the goal of the custom sole member.

Once a design has been generated, as with first custom sole 2300, the sole member may be manufactured. In some embodiments, the modifications may include regions of the sole member with apertures 150 disposed along different portions of the sole member. In some embodiments, a sole member can be molded in a manner that creates apertures in the sole member. An article of footwear including apertures can be formed in any manner. In some embodiments, apertures can be created in a sole member using any known methods of cutting or drilling. For example, in one embodiment, apertures can be created using laser cutting techniques. Specifically, in some cases, a laser can be used to remove material from a sole member in a manner that forms apertures in the sole member. In another embodiment, a hot knife process could be used for forming apertures in a sole member. Examples of methods for forming apertures on a sole member are disclosed in McDonald, U.S. Pat. No. 7,607,241, issued Oct. 27, 2009, titled "Article of Footwear with an Articulated Sole Structure," (previously U.S. patent application Ser. No. 11/869,604, filed Oct. 9, 2007), the entirety of which is hereby incorporated by reference.

In other embodiments, however, any other type of cutting method can be used for forming apertures. Furthermore, in some cases, two or more different techniques can be used for forming apertures. As an example, in another embodiment, apertures disposed on a side surface of a sole member can be formed using laser cutting, while apertures on a lower surface of the sole member could be formed during a molding process. Still further, different types of techniques could be used according to the material used for a sole member. For example, laser cutting may be used in cases where the sole member is made of a foam material.

Figure 25:
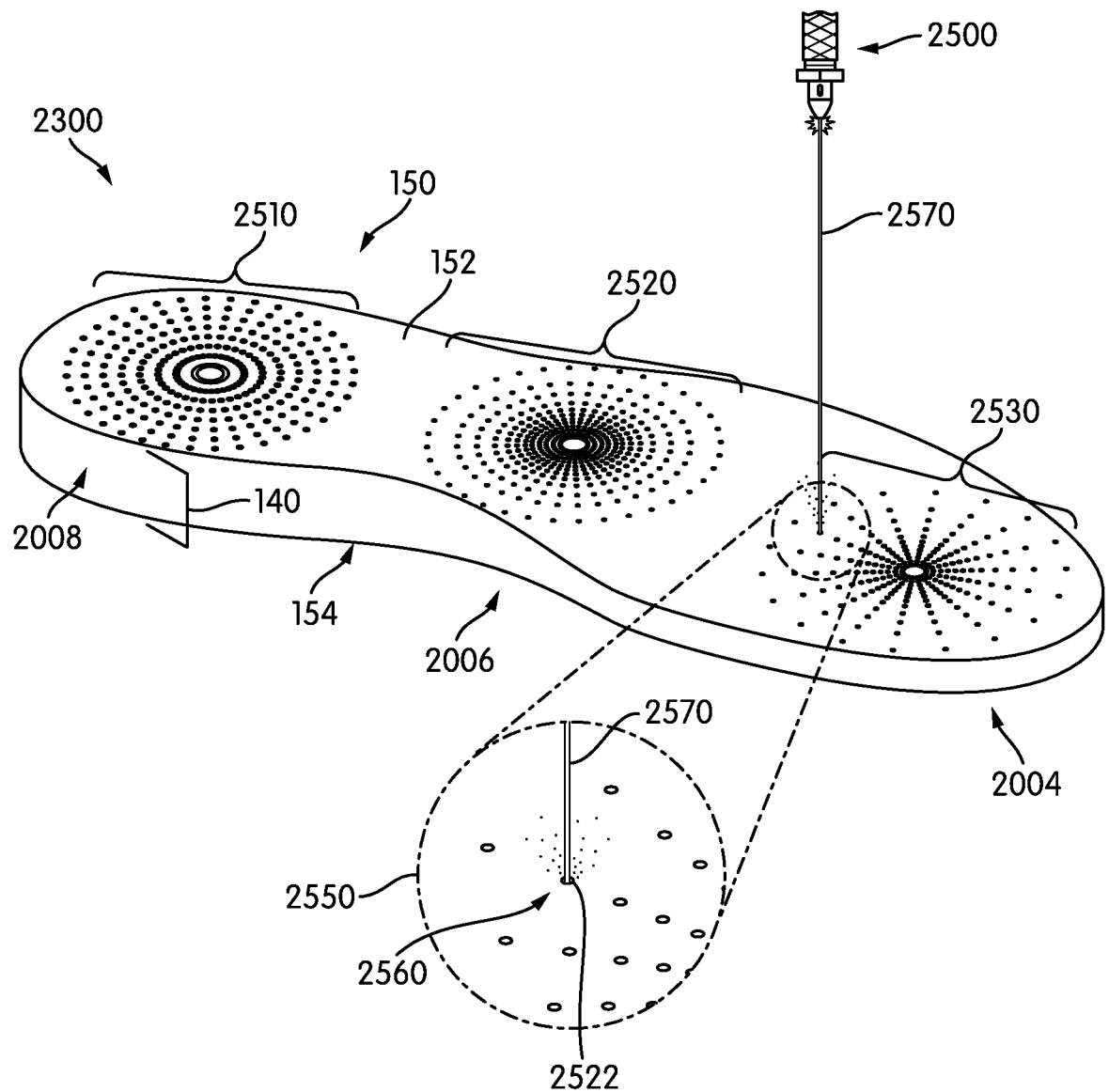
FIG. 25 is an embodiment of an influence diagram.

In FIG. 25, a figure depicting an embodiment of a method of forming first custom sole 2300, including apertures, is shown. Referring to FIG. 25, apertures 150 can be applied to or formed in first custom sole 2300 using a laser drill 2500. In one embodiment, laser drill 2500 may be used to cut away or remove material through thickness 140 of first custom sole 2300. In other cases, there may be a greater number of laser drills used. In FIG. 25, a third group of apertures 2530 along forefoot region 2004 is being formed along a surface of first custom sole 2300. First group of apertures 2510 in heel region 2008 and second group of apertures 2520 in midfoot region 2006 are shown as having been previously formed by laser drill 2500. As an example, first group of apertures 2510 includes an arrangement substantially similar to second pattern 1100 of FIG. 11, and second group of apertures 2520 includes an arrangement substantially similar to third pattern 1200 of FIG. 12. Furthermore, third group of apertures 2530 includes an arrangement substantially similar to fourth pattern 1300 of FIG. 13.

Although only apertures in one general region are shown being drilled in this example, it will be understood that a similar method could be used for creating or forming apertures in any other region of first custom sole 2300. It should further be understood that laser drill 2500 may include provisions for moving along different directions in order to direct the laser beam to the desired location. Furthermore, the sole member may be disposed such that it may be automatically or manually moved to receive a laser 2570 at the appropriate or desired location, such as along forefoot region 2004, midfoot region 2006, and/or heel region 2008. In addition, while only one laser drill 2500 is shown in use in FIG. 25, in other embodiments, two, three, four, or more laser drills may be engaged with the sole member.

In some embodiments, referring to a magnified area 2550, it can be seen that laser 2570 may contact upper surface 152 of first custom sole 2300. When laser 2570 contacts the material, it may begin to remove material and form a hole 2522. As laser 2570 continues to engage with the material of the sole member, hole 2522 may grow through thickness 140 and form a first aperture 2560.

It may be recalled that each aperture may be formed such that they differ in one or more respects from one another, or they may be formed in a uniform manner, such that they are substantially similar in size, length, and shape. Furthermore, it should be understood that laser 2500 may be oriented at an angle different from that shown in FIG. 25, so that laser 2500 can form apertures 150 oriented in a diagonal or non-parallel manner with respect to vertical axis 170, longitudinal axis 180, and/or lateral axis 190.

Thus, as described herein, in some embodiments, the arrangement of apertures on a sole member could be varied to tune properties of the sole member for specific types of physical or personal characteristics, and/or athletic activities, and to provide a particular local cushioning characteristic. For example, in some cases, the arrangement of apertures on a sole member could be selected according to the type of sport for which the article of footwear is intended. In some embodiments, a manufacturer could vary the arrangement of apertures for various types of footwear, including, but not limited to, soccer footwear, running footwear, cross-training footwear, basketball footwear, as well as other types of footwear. Additionally, in other embodiments, the arrangement of apertures on a sole member could be varied according to the gender of the intended user. For example, in some cases, the aperture arrangements may vary between footwear for men and footwear for women. Still further, in some embodiments, the arrangement of apertures on a sole member could be varied according to preferences of a user for achieving desired performance effects. As an example, a desire for increased flexibility on a lateral side of the article can be accommodated by increasing the number and/or size of apertures on the lateral side of the sole member. In addition, in some embodiments, the configuration of apertures on a sole could be varied to achieve various visual or graphical effects. Furthermore, as discussed above, the arrangement of apertures can be individually customized by measuring various pressure regions of a person's foot and applying that information to the positioning and type of apertures on the sole member.

It should be understood that methods of customizing aperture configuration for particular sports, gender, and/or personal preferences can be achieved in any manner. In one embodiment, a method of customizing aperture configuration for an article can include provisions for allowing a user to select a customized aperture arrangement by interacting with a website that provides customization tools for varying the number and/or geometry of various apertures. Examples of different customization systems that can be used for customizing aperture configurations are disclosed in Allen et al., U.S. Patent Publication Number 2005/0071242, published Mar. 31, 2005, titled "Method and System for Custom-Manufacturing Footwear," (previously U.S. patent application Ser. No. 10/675,237, filed Sep. 30, 2003), and Potter et al., U.S. Patent Publication Number 2004/0024645, published Feb. 5, 2004, titled "Custom Fit Sale of Footwear," (previously U.S. patent application Ser. No. 10/099,685, filed Mar. 14, 2002) the entirety of both being hereby incorporated by reference. It will be understood that the method of customizing aperture arrangements for an article of footwear are not limited to use with any particular customization system, and in general any type of customization system known in the art could be used.

Articles of the embodiments discussed herein may be made from materials known in the art for making articles of footwear. For example, a sole member may be made from any suitable material, including, but not limited to, elastomers, siloxanes, natural rubber, other synthetic rubbers, aluminum, steel, natural leather, synthetic leather, foams, or plastics. In an exemplary embodiment, materials for a sole member can be selected to enhance the overall flexibility, fit, and stability of the article. In one embodiment, a foam material can be used with a sole member, as foam can provide the desired elasticity and strength. In another embodiment, a rubber material could be used to make a midsole of a sole member. In still another embodiment, a thermoplastic material could be used with a sole member. For example, in one embodiment, thermoplastic polyurethane (TPU) may be used to make a midsole for a sole member. In still other embodiments, a sole member may comprise a multi-density insert that comprises at least two regions of differing densities. For example, in one other embodiment, a midsole of a sole member could be configured to receive one or more inserts. Examples of different types of inserts that could be used are disclosed in Yu et al., U.S. Pat. No. 7,941,938, issued May 17, 2011, titled "Article of Footwear with Lightweight Sole Assembly," (previously U.S. patent application Ser. No. 11/752,348, filed Mar. 23, 2007), the entirety of which is hereby incorporated by reference. Also, an upper may be made from any suitable material known in the art, including, but not limited to, nylon, natural leather, synthetic leather, natural rubber, or synthetic rubber.

An article of footwear can include provisions for adjusting the flexibility characteristics of a sole member with a plurality of apertures. In some embodiments, different materials can be used with different portions of a sole. In an exemplary embodiment, portions of a sole can be filled with additional material or components to provide different types of cushioning, feel, and flexibility for a sole member. For example, in one embodiment, a core portion of a sole member may comprise a fluid-filled member, such as an air bladder. In another embodiment, one or more portions of a sole member could include hollow cavities capable of receiving fluid or other materials.

An article of footwear can include provisions for adjusting the flexibility characteristics of a sole structure with a plurality of apertures. In some embodiments, different materials can be used with different portions of a sole. In an exemplary embodiment, portions of a sole can be filled with additional material or components to provide different types of cushioning, feel, and flexibility for a sole structure. For example, in one embodiment, a core portion of a sole structure may comprise a fluid-filled member, such as an air bladder. In another embodiment, one or more portions of a sole structure could include hollow cavities capable of receiving fluid or other materials.

Figure 26:
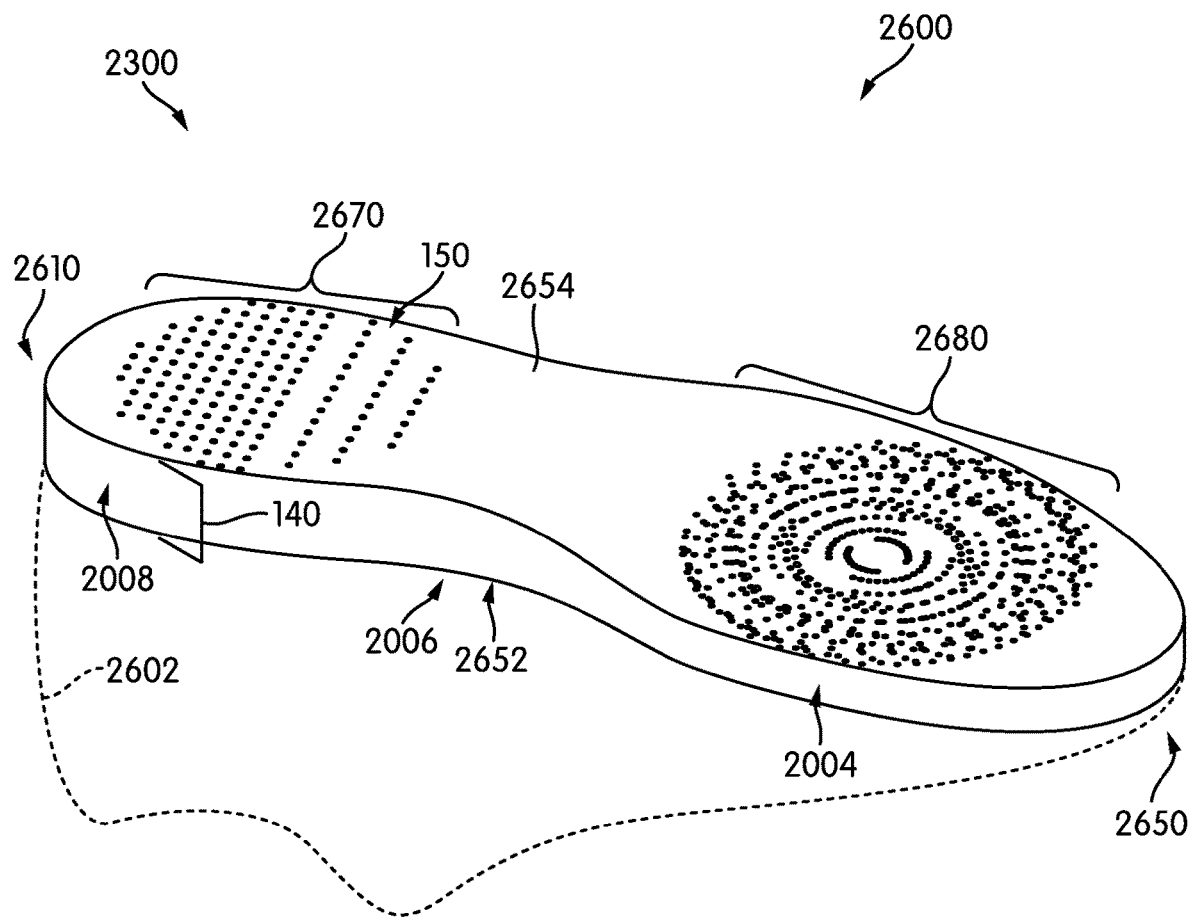
FIG. 26 is an isometric bottom view of an embodiment of an article of footwear with a sole member.

FIG. 26 illustrates another embodiment of a custom sole member for an article of footwear. In FIG. 26, an article of footwear 2600 is shown, hereby referred to as article 2600. Article 2600 can be configured as any type of footwear including, but not limited to, hiking boots, soccer shoes, football shoes, sneakers, rugby shoes, basketball shoes, baseball shoes as well as other kinds of footwear. Article 2600 can comprise an upper 2602 and a sole structure 2610. Sole structure 2610 is secured to upper 2602 and extends between the foot and the ground when article 2600 is worn. In different embodiments, sole structure 2610 may include different components. For example, sole structure 2610 may include an outsole, a midsole, and/or an insole. In some cases, one or more of these components may be optional.

Generally, a customized sole member may comprise any layer or element of sole structure 2610, and be configured as desired. In particular, layers of the sole structure may have any design, shape, size, and/or color. For example, in embodiments where an article of footwear is a basketball shoe, a sole member could include contours shaped to provide greater support to heel prominence. In embodiments where the article of footwear is a running shoe, the custom sole member could be configured with contours supporting forefoot region 2004. In some embodiments, sole structure 2610 could further include provisions for fastening to an upper or another sole layer, and may include still other provisions found in footwear sole members. Also, some embodiments of sole structure 2610 may include other materials disposed within the custom sole member, such as air bladders, leather, synthetic materials (such as plastic or synthetic leather), mesh, foam, or a combination thereon.

The material selected for sole structure 2610 or components of sole structure 2610 may possess sufficient durability to withstand the repetitive compressive and bending forces that are generated during running or other athletic activities. In some embodiments, the material(s) may include foams; polymers such as urethane or nylon; resins; metals such as aluminum, titanium, stainless steel, or lightweight alloys; or composite materials that combine carbon or glass fibers with a polymer material, ABS plastics, PLA, glass-filled polyamides, stereolithography materials (epoxy resins), silver, titanium, steel, wax, photopolymers, and polycarbonate. The customized sole member may also be formed from a single material or a combination of different materials. For example, one side of a custom sole member may be formed from a polymer whereas the opposing side may be formed from a foam. In addition, specific regions may be formed from different materials depending upon the anticipated forces experienced by each region.

In FIG. 26, a bottom isometric view of upper 2602 (in dotted line) with sole structure 2610 is shown, where sole structure 2610 includes a second custom sole 2650. An upper surface 2652 is provided on the upper side of second custom sole 2650, and a lower surface 2654 is provided on the bottom side (i.e., the side that would be facing the ground and/or an outsole when worn by a user). Together, upper surface 2652 and lower surface 2654 comprise an exterior surface of second custom sole 2650. Disposed along various portions of the exterior surface are apertures 150 that extend varying lengths and comprise varying patterns through thickness 140 of second custom sole 2650.

In some embodiments, apertures 150 may be disposed on both upper surface 2652 and lower surface 2654 of second custom sole 2650. In other embodiments, apertures 150 may be disposed on only one surface of second custom sole 2650. In FIG. 26, apertures 150 are formed along lower surface 2654. A seventh pattern 2670 is visible in heel region 2008, and an eighth pattern 2680 is visible medial in a portion of forefoot region 2004. As an example, seventh pattern 2670 includes an arrangement substantially similar to sixth pattern 1900 of FIG. 19, and eighth pattern 2680 includes an arrangement substantially similar to fifth pattern 1400 of FIG. 14. In other embodiments, any other regular or irregular pattern may be included in second custom sole 2650. Furthermore, any of the aperture patterns described herein may be enlarged or shrunk (i.e., such that the sizes of each aperture in the pattern are increased or decreased proportionally) to include different-sized patterns in a sole member. In other words, in some embodiments, a sole member may include a portion of a single pattern that is enlarged to extend over the entirety of the sole member. In another embodiment, a single pattern may be reduced in size to correspond to the big toe region of the sole member. In other embodiments, any pattern may be resized to be formed along any portion of a sole member. In one embodiment, any of the patterns may be only partially formed on a sole member.

As noted above, apertures 150 may be arranged to correspond to and/or support the contours of plantar surface 2002 of foot 2000 (as described above with reference to FIGS. 20-23). Thus, second custom sole 2650 can provide both general cushioning throughout forefoot region 2004 and heel region 2008, as well as more specialized cushioning in regions where apertures are disposed in particular arrangements (as discussed previously).

Thus, the various cushioning elements as described here can provide a custom sole structure with specialized responses to ground reaction forces. In one embodiment, the cushioning element may attenuate and distributes ground reaction forces. For example, when a portion of the custom sole structure contacts the ground, the apertures disposed in the cushioning element can help attenuate the ground reaction forces. The cushioning element may have the capacity to distribute the ground reaction forces throughout a substantial portion of the custom sole structure. The attenuating property of this type of structure can reduce the degree of the effect that ground reaction forces have on the foot, and the distributive property distributes the ground reaction forces to various portions of a foot. In some embodiments, such features may reduce the peak ground reaction force experienced by the foot.

In other embodiments, cushioning element designs disclosed in this description may also include provisions to achieve a non-uniform ground reaction force distribution. For example, the ground reaction force distribution of a custom sole structure could provide a wearer with a response similar to that of barefoot running, but with attenuated ground reaction forces. That is, the custom sole structure could be designed to impart the feeling of barefoot running, but with a reduced level of ground reaction forces. Additionally, in another example, the ground reaction forces could be more concentrated in the medial side of a foot than along the lateral side of the foot, thereby reducing the probability that the foot will over-pronate, or imparting greater resistance to eversion and inversion of the foot.

In some embodiments, the use of cushioning elements in orthotics for an article of footwear can help support weakened areas of a foot and assist the user in each step. While a relatively rigid material, as may be included in a custom sole structure, can provide functional support to the foot, softer or more flexible regions associated with apertures 150 can absorb the loads put on the foot and provide protection. Such softer or cushioned regions can better absorb the loads placed on a foot, increase stabilization, and take pressure off uncomfortable or sore spots of the feet.

Other embodiments or variations of custom sole structures may include other lattice structure designs or various combinations of the above-disclosed designs. It should be noted that the present description is not limited to cushioning elements having the geometry or aperture configurations of first custom sole 2300 or second custom sole 2650. In different embodiments, each customized sole structure may include further variations not depicted in the figures. Some variations may include differences in shape, size, contour, elevations, depressions, curvatures, and other variations. In other words, the custom sole structures depicted herein are merely intended to provide an example of the many types of cushioning element-based sole structure configurations that fall within the scope of the present discussion.

Figure 27:
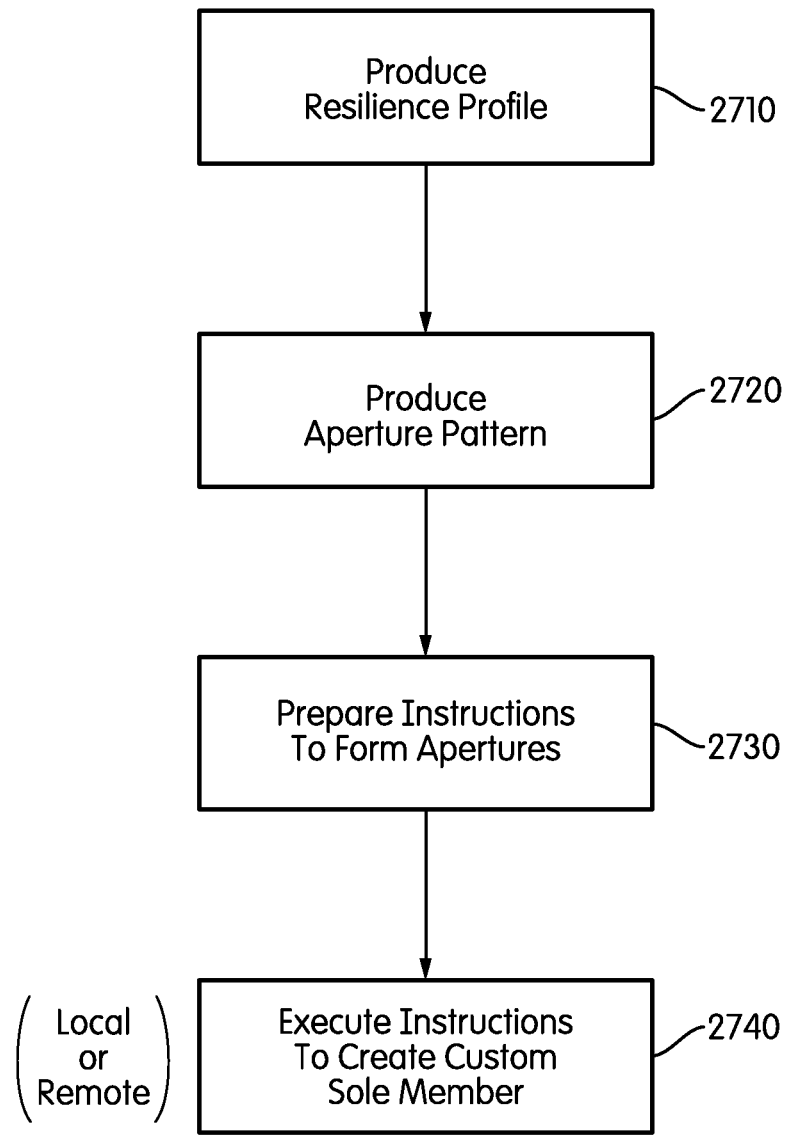
FIG. 27 is an embodiment of a flow chart for a method of making a custom sole member.

An embodiment of the sole member production process as described herein is outlined in the flow chart of FIG. 27. In a first step 2710, a pressure distribution of a user's feet is obtained (see FIGS. 20-23 above). In other words, the pressure distributions associated with a user's left foot and/or a right foot (i.e., a first foot and a second foot) may be obtained. The pressure distributions as well as any other preferences are collected to generate a resiliency profile. In a second step 2720, the resiliency profile may be used to produce a custom configuration or pattern of apertures (e.g., position, size, lengths, orientation, etc.) in a sole member. The particular configuration of apertures generated may be stored in a virtual or digital form in some embodiments. It should be understood that in some embodiments, a first pattern of apertures may be produced for a left foot, and a second pattern of apertures may be produced for a corresponding right foot. Following the production of one or more aperture patterns, instructions to form the apertures in a sole member may be prepared or generated in a third step 2730. In some cases, the aperture pattern may be converted into a series of commands or instructions for a system to follow in order to translate the aperture pattern into mechanical or design steps for forming the customized sole member. Finally, in a fourth step 2740, the instructions are executed and a custom sole member is produced. In some embodiments, the instructions may be executed to produce a first custom sole member (e.g., for a left foot) and a complementary second custom sole member (e.g., for a right foot).

The process described herein may occur in rapid succession and in close proximity to one another in some embodiments. However, in other embodiments, one or more steps may occur spaced apart in time and location. In other words, one step may occur in a first location, and another step may occur in a second location, where the first location is different from the second location. For example, the resiliency profile of first step 2710 may be produced off-site (e.g., at a shopping outlet or a medial office, etc.), and the aperture pattern of second step 2720 may be produced in a manufacturing facility. In another example, the instructions for forming the apertures of third step 2730 may be prepared or generated in a local site, while the actual production of the custom sole member of fourth step 2740 may occur in a remote site (e.g., out of state, or abroad).

In different embodiments, sole members as well as any apertures in the sole members discussed herein may be formed using any other method known in the art. In some embodiments, any removal process (i.e., where a portion of a material is removed, subtracted, eliminated, etc.) may be used to form one or more apertures (e.g., apertures 150). For example, in some embodiments, a mechanical process may be used, including but not limited to ultrasonic machining, water jet machining, abrasive jet machining, abrasive water jet machining, ice jet machining, and/or magnetic abrasive finishing. In other embodiments, chemical processes may be utilized, including but not limited to chemical milling, photochemical milling, and/or eletropolishing. Furthermore, in some embodiments, electrochemical processes may be used. In other embodiments, thermal processes can be used, such as electrodischarge machining (EDM), laser beam machining, electron beam machining, plasma beam machining, and/or ion beam machining, or other processes. In another embodiment, hybrid electrochemical processes can be utilized, including but not limited to electrochemical grinding, electrochemical honing, electrochemical superfinishing, and/or electrochemical buffing. In addition, hybrid thermal processes may be used, such as electroerosion dissolution machining. In other embodiments, the material comprising the sole member may be modified using chemical processes, including temperature changes (e.g., freezing the material). Furthermore, the processes for forming the apertures may be applied or utilized after the article of footwear has been assembled, or the sole member has been associated with an upper or sole structure. In other words, the formation of apertures in a sole member may occur post-manufacturing of the article of footwear.

It should be understood that in other embodiments, the midsole can include a casing in a molded foam. In other words, embodiments of the sole member as described herein may be associated with the midsole of a sole structure. Thus, in some embodiments, a midsole may include a foam material. The foam material can comprise a 'skin' surface that is formed from a molding process. In some embodiments, the various removal processes described above (e.g., drilling, laser, chemical, EDM, water cutting, etc.) can be applied to the foam skin of a midsole and apertures can be formed in a manner similar to the embodiments discussed above.

While various embodiments have been described, the description is intended to be exemplary, rather than limiting, and it will be apparent to those of ordinary skill in the art that many more embodiments and implementations are possible that are within the scope of the embodiments. Although many possible combinations of features are shown in the accompanying figures and discussed in this detailed description, many other combinations of the disclosed features are possible. Any feature of any embodiment may be used in combination with or substituted for any other feature or element in any other embodiment unless specifically restricted. Therefore, it will be understood that any of the features shown and/or discussed in the present disclosure may be implemented together in any suitable combination. Accordingly, the embodiments are not to be restricted except in light of the attached claims and their equivalents. Also, various modifications and changes may be made within the scope of the attached claims.

What is claimed is:

1. A sole member for an article of footwear, comprising:
   an outer surface comprising an upper surface and a lower surface; and
   an interior portion disposed between the upper surface and the lower surface,
   wherein a first set of apertures is formed in the sole member in a first pattern, wherein the first set of apertures includes more than 100 apertures formed as a plurality of parallel rows of apertures, wherein the plurality of parallel rows of apertures includes: (a) a first row of apertures arranged in a linear configuration, (b) a second row of apertures arranged in a linear configuration, (c) a third row of apertures arranged in a linear configuration, and (d) a fourth row of apertures arranged in a linear configuration, and wherein the first set of apertures is formed in a heel region of the sole member, and
   wherein a second set of apertures is formed in a forefoot region of the sole member in a second pattern, wherein the second set of apertures includes more than 100 apertures formed as a plurality of rings of apertures, wherein the plurality of rings of apertures includes: (a) a first ring of apertures located a first radial distance from a first center and (b) a second ring of apertures located a second radial distance from the first center and wherein the first radial distance differs from the second radial distance.

2. The sole member according to claim 1, wherein the first row of apertures lies immediately adjacent the second row of apertures, wherein the first row of apertures is separated from the second row of apertures by a first distance, wherein the third row of apertures lies immediately adjacent the fourth row of apertures, wherein the third row of apertures is separated from the fourth row of apertures by a second distance, and wherein the first distance is greater than the second distance.

3. The sole member according to claim 2, wherein the third row and the fourth row are located further rearward in the sole member than the first row and the second row.

4. The sole member according to claim 1, wherein the sole member comprises a foam material, and wherein the first set of apertures is formed in the foam material.

5. The sole member according to claim 4, wherein aperture position, size, length, and orientation in the first pattern of the first set of apertures are customized for a wearer based on information obtained about a pressure distribution of a wearer's foot.

6. The sole member according to claim 1, wherein aperture position, size, length, and orientation in the first pattern of the first set of apertures are customized for a wearer based on information obtained about a pressure distribution of a wearer's foot.

7. A sole member for an article of footwear, comprising:
   an outer surface comprising an upper surface and a lower surface; and
   an interior portion disposed between the upper surface and the lower surface,
   wherein a first set of apertures is formed in the sole member in a first pattern, wherein the first set of apertures includes more than 100 apertures formed as a plurality of parallel rows of apertures, wherein the plurality of parallel rows of apertures includes: (a) a first row of apertures arranged in a linear configuration, (b) a second row of apertures arranged in a linear configuration, (c) a third row of apertures arranged in a linear configuration, and (d) a fourth row of apertures arranged in a linear configuration,
   wherein a second set of apertures is formed in the sole member spaced apart from the first set of apertures, wherein the second set of apertures is formed in the sole member in a second pattern, wherein the second set of apertures includes more than 100 apertures formed as a plurality of rings of apertures, wherein the plurality of rings of apertures includes: (a) a first ring of apertures located a first radial distance from a first center and (b) a second ring of apertures located a second radial distance from the first center, and wherein the first radial distance differs from the second radial distance.

8. The sole member according to claim 7, wherein the sole member comprises a foam material, and wherein the first set of apertures and the second set of apertures are formed in the foam material.

9. A sole member for an article of footwear, comprising:
   an outer surface comprising an upper surface and a lower surface; and
   an interior portion disposed between the upper surface and the lower surface,
   wherein a first set of apertures is formed in the sole member in a first pattern, wherein the first set of apertures includes more than 100 apertures formed as a plurality of rings of apertures, wherein the plurality of rings of apertures in the first set of apertures are arranged along the outer surface in a generally round and circular pattern around a first center, wherein the plurality of rings of apertures includes: (a) a first ring of apertures located a first radial distance from the first center and (b) a second ring of apertures located a second radial distance from the first center, and wherein the first radial distance differs from the second radial distance.

10. The sole member according to claim 9, wherein the sole member comprises a foam material, and wherein the first set of apertures is formed in the foam material.

11. The sole member according to claim 9, wherein the first set of apertures is formed in a forefoot region of the sole member.

12. The sole member according to claim 11, wherein a second set of apertures is formed in a heel region of the sole member, wherein the second set of apertures is formed in the sole member in a second pattern, wherein the second set of apertures includes more than 100 apertures formed as a plurality of rows of apertures.

13. The sole member according to claim 12, wherein the sole member comprises a foam material, and wherein the first set of apertures and the second set of apertures are formed in the foam material.

14. The sole member according to claim 11, wherein a second set of apertures is formed in a heel region of the sole member in a second pattern, wherein the second set of apertures includes more than 100 apertures formed as a plurality of parallel rows of apertures, wherein the plurality of parallel rows of apertures includes: (a) a first row of apertures arranged in a linear configuration extending across a width direction of the sole member, (b) a second row of apertures arranged in a linear configuration extending across the width direction of the sole member, (c) a third row of apertures arranged in a linear configuration extending across the width direction of the sole member, and (d) a fourth row of apertures arranged in a linear configuration extending across the width direction of the sole member.

15. The sole member according to claim 14, wherein the sole member comprises a foam material, and wherein the first set of apertures and the second set of apertures are formed in the foam material.

16. The sole member according to claim 9, wherein the first pattern of the first set of apertures is customized for a wearer based on information obtained about a pressure distribution of the wearer's foot.

\* \* \* \* \*